United States Patent [19]

Williams et al.

[11] Patent Number: 4,766,064

[45] Date of Patent: * Aug. 23, 1988

[54] DISPLACEMENT POLYNUCLEOTIDE ASSAY EMPLOYING POLYETHER AND DIAGNOSTIC KIT

[75] Inventors: Jon I. Williams, Montclair; Marian S. Ellwood, Summit, both of N.J.; Mary Collins, Natick; Edward F. Fritsch, Concord, both of Mass.; Joseph G. Brewen, Convent Station; Steven E. Diamond, Springfield, both of N.J.

[73] Assignees: Allied Corporation, Morristown, N.J.; Genetics Institute, Inc., Cambridge, Mass.

[*] Notice: The portion of the term of this patent subsequent to May 29, 2001 has been disclaimed.

[21] Appl. No.: 684,308

[22] Filed: Dec. 20, 1984

Related U.S. Application Data

[63] Continuation-in-part of Ser. No. 607,885, May 7, 1984.

[51] Int. Cl.[4] ............ C12Q 1/68; G01N 33/566
[52] U.S. Cl. ................ 435/6; 435/803; 435/810; 935/78; 436/501
[58] Field of Search ............ 935/3, 6, 9, 10, 76, 935/77, 78; 436/94, 501, 518, 538, 541, 542, 824, 826, 539; 536/27; 435/6, 803, 810

[56] References Cited

U.S. PATENT DOCUMENTS

| | | |
|---|---|---|
| 3,798,320 | 3/1974 | Weiss ............ 435/803 |
| 4,205,952 | 6/1980 | Cais ............ 436/518 |
| 4,302,204 | 11/1981 | Wahl ............ 436/501 |
| 4,358,535 | 11/1982 | Falkow et al. ............ 435/5 |
| 4,388,295 | 6/1983 | Cocola et al. ............ 424/1 |
| 4,434,236 | 2/1984 | Freytag ............ 436/512 |
| 4,486,539 | 12/1984 | Ranki et al. ............ 436/504 |
| 4,629,689 | 12/1986 | Diamond et al. ............ 436/63 X |

FOREIGN PATENT DOCUMENTS

| | | |
|---|---|---|
| 0063879 | 11/1982 | European Pat. Off. . |
| 0070687 | 1/1983 | European Pat. Off. . |
| 0097373 | 1/1984 | European Pat. Off. . |
| 0124221 | 11/1984 | European Pat. Off. . |
| 0133288 | 2/1985 | European Pat. Off. . |
| 0139489 | 5/1985 | European Pat. Off. . |

OTHER PUBLICATIONS

Green, C. et al., *Nucleic Acids Research*, vol. 9, No. 8, 1981, pp. 1905-1918.

Pheiffer, B. H. et al., *Nucleic Acids Research*, vol. 11, No. 22, 1983, pp. 7853-7871.

Renz, M. et al., *Nucleic Acids Research*, vol. 12, No. 8, 1984, pp. 3435-3444.

Ingham, K. C., "Polyethylene Glycol in Aqueous Solution: Solvent Perturbation and Gel Filtration Studies", pp. 59-68 (1977).

Galfre, G. et al., "Antibodies to Major Histocompatibility Antigens Produced by Hybrid Cell Lines", pp. 550-552, Nature, vol. 226.

Zimmerman, S. B. et al., "Macromolecular Crowding Allows Blunt-End Ligation by DNA Ligases from Rat Liver or *Escherichia coli*", pp. 5852-5856, Pro. Natl. Acad. Sci., vol. 80, Oct. 1983.

(List continued on next page.)

Primary Examiner—Charles F. Warren
Assistant Examiner—Jeremy M. Jay
Attorney, Agent, or Firm—Alan M. Doernberg

[57] ABSTRACT

A diagnostic reagent is disclosed containing a complex of a probe polynucleotide (P) bound via purine/pyrimidine hydrogen bonding to a labeled polynucleotide (L). The probe (P) contains a target binding region (TBR) capable of binding to a target nucleotide sequence (G) of a biological sample. A method is disclosed in which contact with a sample containing the target nucleotide sequence (G) causes binding, initially between G and a single-stranded portion (IBR) of the target binding region (TBR). Thereafter the labeled polynucleotide (L) is displaced from the complex by branch migration of (G) into the (P)/(L) binding region. A volume excluding polymeric agent such as poly(ethylene oxide) (PEO or PEG) or other polyethers enhances the rate of appearance of displaced labeled polynucleotide. Determination of displaced labeled polynucleotide (L) gives a value which is a function of the presence and concentration of target nucleotide sequence (G) in the sample.

31 Claims, 3 Drawing Sheets

OTHER PUBLICATIONS

Wetmur, J. G., "Excluded Volume Effects on the Rate of Renaturation of DNA", pp. 601-613, Biopolymers, vol. 10 (1971).

Wahl, G. M. et al., "Efficient Transfer of Large DNA Fragments from Agarose Gels to Diszobenzyloxymethyl-Paper and Rapid Hybridization by Using Dextran Sulfate", Proc. Natl. Acad. Sci., vol. 76, No. 8, pp. 3683-3687, Aug. 1979.

Yamamoto, K. R. et al., Virology 40, 734-44 (1970); "Rapid Bacteriophase Sedimentation in the Presence of Polyethylene Glycol and Its Application to Large-Scale Virus Purification".

Alberts, B. M., *Methods in Enzymology*, S. P. Colowick and N. O. Kaplans, eds. Academic Press, NY, vol. 12, pp. 566-581 (1967); Chapter entitled, "Fractionation of Nucleic Acids by Dextran-Polyethylene Glycol Two-Phase Systems".

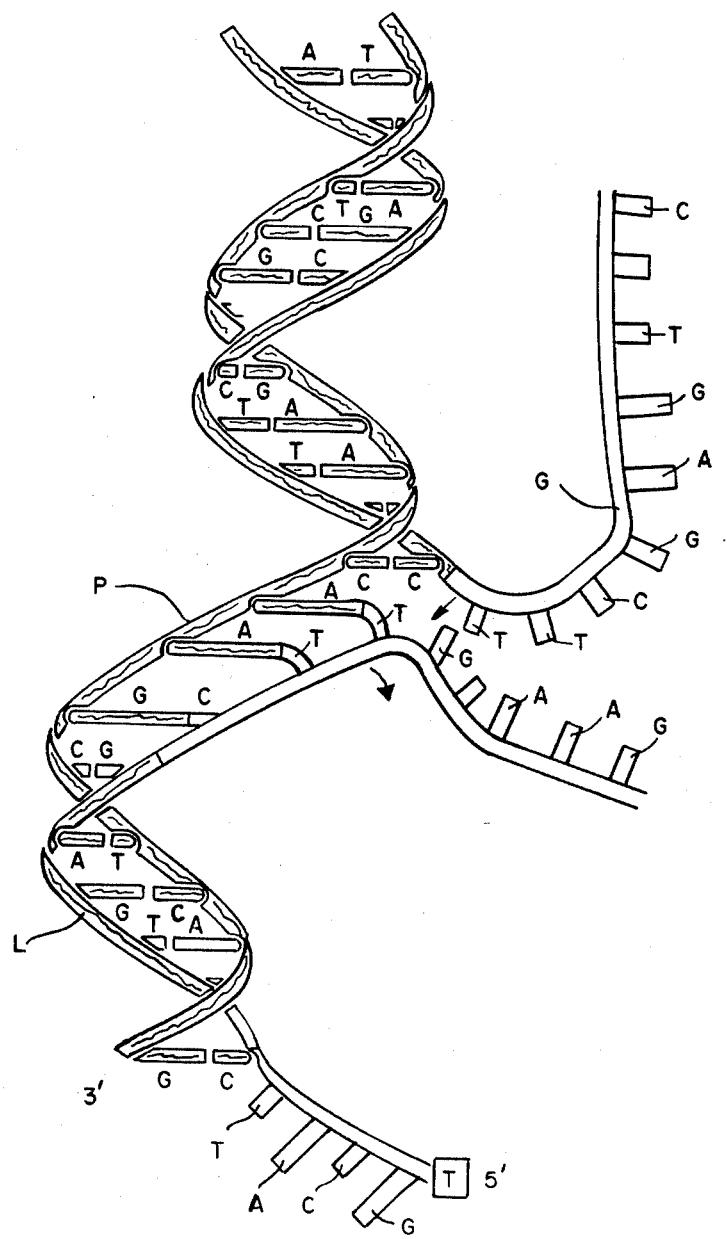
FIG. ID

DISPLACEMENT POLYNUCLEOTIDE ASSAY EMPLOYING POLYETHER AND DIAGNOSTIC KIT

This is a continuation-in-part of U.S. Ser. No. 607,885, filed May 7, 1984, entitled "Displacement Polynucleotide Assay Method and Polynucleotide Complex Reagent Therefor", which is copending and commonly assigned, the disclosure of which is incorporated herein by reference.

BACKGROUND OF THE INVENTION

The present invention relates to a diagnostic assay method and kit for detecting the presence of a target nucleotide sequence (either DNA or RNA) in a biological sample.

Conventional methods for detecting the presence of a particular polynucleotide in a biological sample typically involve immobilization of nucleic acid of the sample on a surface as the initial step. Once the sample is immobilized, a probe polynucleotide strand, usually tagged with a detectable label such as radioactive phosphorus atoms, is incubated with the immobilized sample so as to bind to the immobilized sample by purine/pyrimidine base sequence-specific complementary base pairing when the immobilized sample contains the target nucleotide sequence. After washing off the labeled probe which has not so hybridized, the presence or absence of label on the support is then determined. Techniques for this determination include exposure of a photographic film, liquid scintillation counting, and fluorescence microscopy. See U.S. Pat. No. 4,358,535 to Falkow et al. (1982).

Ward and coworkers (see EPA No. 63,879 (1982)) have described a variation of this technique in which, rather than tagging the probe directly with a detectable label, the probe is tagged with a nonisotopic substituent such as biotin on certain nucleotides. In such case, after the unhybridized probe is washed off, the support is contacted with a reagent such as avidin linked to an enzyme. The avidin-enzyme complex binds selectively to biotin because of the high avidin-biotin binding affinity, so as to affix enzyme selectively where the target nucleotide sequence has been immobilized on the support. Thereafter, a substrate for the enzyme is added and products of the enzymatic reaction are detected, yielding an amplified signal functionally dependent upon the initial concentration of target nucleotide sequence on the support. See also EPA No. 97,373 of ENZO BIOCHEM, INC (Jan. 4, 1984).

A variation in the above nonisotopic system has also been described in another European patent application of Standard Oil of Illinois (EPA No. 70,687 (1983)) in which, in one form (see pages 8-10 thereof), two nucleic acid probes specific for the target nucleotide sequence are employed. The first probe, which can hybridize to a first portion of the target nucleotide sequence, is affixed to a solid support such that, upon incubation of the solid support with a sample of the biological material, target nucleotide sequences in the sample will bind to the support selectively via this first immobilized probe. Thereafter or concurrently, the second probe, which can hybridize selectively to a second and distinct portion of the target nucleotide sequence, is exposed to the support. Again, if the target nucleotide sequence is present in the biological sample, the second probe will bind selectively to that nucleotide sequence; and a combination structure (or sandwich) will be created linking the second probe to the support via the first probe and the target nucleotide sequence. The published patent application discloses labeling this second probe with a moiety directly or indirectly generating or absorbing specific wavelengths of light (e.g., a fluorescent label, a phosphorescent label or a chemiluminescent label). By separating the support from unbound solution constituents at each stage, the presence of label in the phase with support after the third separation will be a function of the presence and concentration of the target nucleotide sequence in the sample. See also WO No. 83/01459 of Orion-Yhtma Oy (Apr. 29, 1983).

While the above hybridization procedures will detect the presence of target nucleotide sequences in biological samples in many cases, they each have the disadvantage of either multiple steps or steps with necessarily long incubation periods that make them impracticable for easy use in a clinical laboratory. Furthermore, many of these processes suffer from a limited selectivity or sensitivity with regard to interfering polynucleotide sequences or reliable detection of low levels of target nucleotide sequence against the background signal. In particular, nonspecific binding of the labeled probe represents a substantial source of background signal in each process.

Apart from the analysis of biological samples for target nucleotide sequences, various aspects of the physical chemistry of hybridization (formation of double-stranded helices between complementary polynucleotide sequences) have been studied. These studies have included examination of the phenomena of strand migration and displacement in nucleic acid, both in vivo and in vitro. By referring to such studies, however, we do not admit that the phenomena of strand migration and displacement have any obvious applicability to diagnosis and detection. C. Green and C. Tibbetts, *Nucleic Acids Research* vol. 9, No. 8, pp. 1905-18 (1981), have described the formation of a complex (hybrid) of a 6.1 kb (6100 base long) single-stranded DNA polynucleotide hybridized near its middle (the interval 1.7-3.3 kb) to an end-labeled complementary DNA polynucleotide of 1.6 kb length. Addition to this complex, in solution, of the 6.1 kb complementary strand caused rapid displacement of the labeled polynucleotide (see FIG. 2 on page 1910 of this reference), monitored by taking aliquots of the reaction mixture, separating then by gel chromatography and analyzing then by autoradiography. The displaced 1.6 kb polynucleotide increased steadily from under 10% to over 90% of the radioactive signal in a period of more than 85 minutes (depending upon concentration) with the 1.6/6.1 kb hybrid accounting for the bulk of the remaining radioactivity. The presumed partially displaced intermediate, which would have a total mass equivalent to 13.8 kb of DNA (both long strands and a partially displaced short strand) was apparently not detected. The authors concluded that the initial hybridization of the two 6.1 kb polynucleotides, forming a branched species, was the rate-limiting step; and that displacement along the 1.6 kb paired region of a labeled polynucleotide was very rapid, consistent with a calculated average lifetime of the branched (13.8 kb mass equivalent) species of 0.8 minutes. They indicate the possibility of both single-branched or doubly nucleated (D-looped) intermediate species (illustrated on page 1912 of the reference). In order to better study the phenomenon of branch migration, they attempted to slow the displacement process, by using drugs which might retard the migration phenomenon and/or by using complexes with more than 1.6 kb of hybrid base pairing (see pages 1913–1914 of the reference). It should be noted that the 1.6/6.1.kb species was challenged by Green et al only with the 6.1 kb complementary strand, purified away from any non-specific strands.

A separate issue in nucleic acid biochemistry has been the examination of polymeric species which interact with nucleic acids during strand hybridization processes. Polyethers such as poly(ethylene glycol) have found use in a variety of specific biological or biochemical processes such as viral particle isolation (K. R. Yamamoto et al., *Virology* 40,734–744 (1970)), nucleic acid purification (B. Alberts in *Methods in Enzymology*, S. P. Colowick and N. O. Kaplans, eds. (Academic Press, N.Y.), vol. 12, pp. 566–581 (1967)), protein purification (K. G. Ingram, *Arch. Biochem. Biophys.* 184, 59–68 (1977)), mammalian cell fusion (G. Galfre et al., *Nature* 266, 550–552 (1977)) and enhancement of specific enzymatic activity (B. H. Pfeiffer and S. B. Zimmerman, *Nucleic Acids Research* 11,7853–7871 (1983)). M. Renz and C. Kurz, *Nucleic Acids Research*, vol. 12, 3435–44 (1984) (which may not constitute prior art with respect to the present invention) disclose the use of polyethylene glycol as a volume excluding agent to enhance the rate of hybridization in an immobilized-sample type of DNA probe assay (particularly of the type referred to as a Southern blot). See especially page 3441 of this reference. In this respect other volume exclusion polymers of various types have been shown to enhance the rate of hybridization of matched single strands. See Wetmur et al., *Biopolymers*, vol. 10, pp. 601–613 (1971) (dextran sulfate), Wahl et al., Proc. Nat. Acad. Sci., vol. 76, pp. 3683 (dextran sulfate). In general, polymers useful in this regard are non-ionic or anionic water-soluble polymers (including polysaccharides) which do not react with DNA. See S. B. Zimmerman et al, *Proc. Nat. Acad. Sci.*, vol. 80, 5852–56 (1983); B. H. Pfeiffer et al, cited above; *Water-soluble Synthetic Polymers* (P. Molyneux, ed.; CRC Press, Inc., Cleveland, Ohio—two volumes, 1983).

BRIEF DESCRIPTION OF THE INVENTION

The present invention is based upon the rapid displacement of a labeled polynucleotide from a probe polynucleotide by the target nucleotide sequence of a sample, with the appearance of displaced labeled polynucleotide being enhanced by the presence of a volume excluding polymer agent such as poly(ethylene glycol), enabling direct or indirect measurement of label found in or on the displaced labeled polynucleotide (or in some cases the labeled polynucleotide not displaced). This label serves as a reliable and quantitative measurement functionally related to the presence and concentration of target nucleotide sequence in a sample. Accordingly, the present invention provides a method for determining the presence of a predetermined target nucleotide sequence (either DNA or RNA) in the nucleic acid of a biological sample which comprises the steps:

(a) providing a reagent complex of (i) a probe polynucleotide which is capable of base pair binding via hydrogen bonds of purine/pyrimidine base pairs to the target nucleotide sequence, and (ii) a labeled polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the target nucleotide sequence;

(b) contacting the reagent complex with a sample in the presence of a polyether polymer under conditions in which the target nucleotide sequence, if present, binds to the probe polynucleotide and displaces labeled polynucleotide from the reagent complex, the polyether polymer being of a molecular weight and at a concentration sufficient to increase the rate of appearance of specifically displaced labeled polynucleotide; and (c) determining the presence (which can include determining the amount) either of labeled polynucleotide displaced from the reagent complex or of the labeled polynucleotide remaining in the reagent complex.

The present invention also provides a diagnostic kit for determining the presence of a target nucleotide sequence in the nucleic acid of a biological sample comprising:

(a) the reagent complex of:

(i) a probe polynucleotide which is capable of binding via hydrogen bonds of purine/pyrimidine base pairs to the target nucleotide sequence, and (ii) a labeled polynucleotide which is bound via hydrogen bonds of purine/pyrimidine base pairs to the probe polynucleotide in a region of the probe polynucleotide at least partially coextensive with the region in which the probe polynucleotide is capable of binding to the target nucleotide sequence;

The base pairing between the target nucleotide sequence and the probe polynucleotide being of sufficient cumulative binding strength (as defined below) for the target nucleotide sequence, if present in a sample with which the reagent is contacted, to be able to displace labeled polynucleotide from the reagent complex; and (b) a polyether polymer of sufficient molecular weight and amount relative to the reaction solution volume to increase the rate of appearance of specifically displaced labeled polynucleotide (due to interactions with appropriate target nucleotide sequences, if present).

The present invention further includes such a method or such a diagnostic kit wherein a volume excluding inert polymer which is non-ionic or anionic (but which is not necessarily a polyether) is present in such amounts sufficient to increase the rate of appearance of displaced labeled polynucleotide.

This effect, increasing the rate of appearance of specifically displaced polynucleotide, is sometimes referred to in the description that follows as an increasing rate of displacement. In such event, that nomenclature should not be read as implying that the actual displacement step is expedited on a microscopic level. In fact, Applicants currently believe that the initial nucleation stage in hybridization of competitor strand to the probe polynucleotide (see FIGS. 1A and 1B) is the rate-limiting step which is enhanced by volume excluding polymer. If that is true, then no enhancement of the displacement step (cf. FIGS. 1C, 1D and 1E) is required on a microscopic level to achieve an increase in the overall rate (compare FIG. 1A to FIG. 1E).

BRIEF DESCRIPTION OF THE FIGURES

FIG. 1D is an enlarged view, similar to FIG. 1C, in which the helical structure of double-stranded portions is schematically shown;

DETAILED DESCRIPTION OF THE INVENTION

Figure 1A:
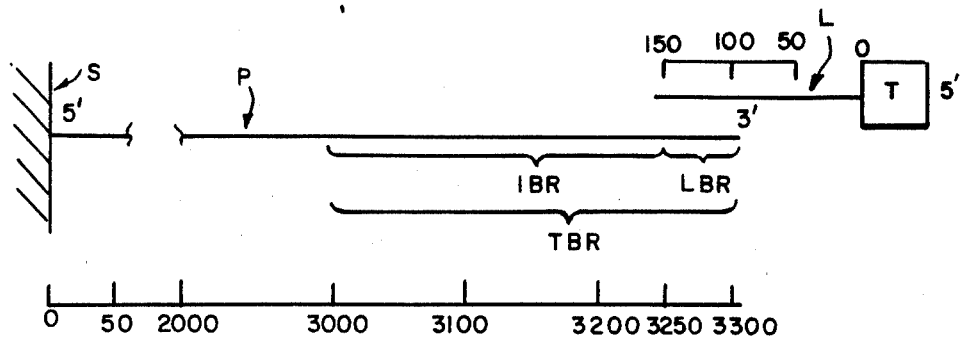
FIG. 1A is a schematic view of one embodiment of the reagent complex of the present reagent useful in the present process.

In this application the following terms are used based on their generally accepted meanings in the field of molecular biology:

Polynucleotide or Polynucleotide Strand refers to a linear polymeric structure of pentose sugars (generally ribose or deoxyribose) linked to each other by 3',5'-phosphodiester linkages, and linked by carbon-nitrogen bonds at the 1-carbon of the sugar to pendant purine or pyrimidine bases such as, but not limited to, uracil (linked naturally to ribose only as rU), thymine (linked naturally to deoxyribose only as dT), cytosine (dC or rC), adenine (dA or rA) and guanine (dG or rG). Polynucleotides thus include strands of deoxyribonucleic acid (DNA) and strands of ribonucleic acid (RNA) or continuous heteropolymers of both types of polynucleotides.

The ends of such Polynucleotide Strands are referred to as the Five Prime (5') ends, where the 5-carbon of the pentose is not linked to another pentose (but may bear hydroxyl, monophosphate or other natural or synthetic moieties), or the Three Prime (3') ends, where the 3-carbon of the pentose is not linked to another pentose (but may similarly bear hydroxyl, monophosphate or other natural or synthetic moieties).

Complementary Base Pairing or Purine/Pyrimidine Base Pairing refers to the hydrogen bonding between opposite bases pendant on two antiparallel Polynucleotide Strands, which is most energetically favorable for natural DNA when dG is opposite dC and dA is opposite dT. Bases other than the five naturally-prevalent ones also have preferential pairing: for example, 5-methylcytosine binds preferentially to guanine. For illustrative purposes, this pairing is shown in many of the Figures by parallel straight lines with complementary strands directed in antiparallel directions (in the 5' to 3' sense). It should be appreciated, however, that the actual geometry of double-stranded segments will normally be helical (the well-known double helix) of various pitches, as schematically illustrated in FIG. 1D.

Hybridization is used herein to refer to admixing two Polynucleotides under conditions conducive to the formation of double-stranded structures, with Complementary Base Pairing causing such double stranded structures to form where complementary sequences or nearly complementary sequences are present.

The basic components of the method of the invention are a probe polynucleotide (sometimes called herein the probe), a labeled polynucleotide (sometimes called herein tagged polynucleotide or release tag), a volume excluding polymer such as a polyether compound and the biological sample containing nucleic acid, a portion of which is sometimes called herein the target polynucleotide or target nucleotide sequence. A sample may or may not contain a target nucleotide sequence. In some cases a support is also provided, either to which the reagent complex is immobilized via the probe (such that the probe is sometimes called an immobilized probe or immobilized probe polynucleotide), or in other cases as a part of the separation step that may follow displacement as a part of the determination or detecting step. In practicing the process, additional reagents or equipment are frequently required for readout; the term readout refers to the direct or indirect detection of labeled polynucleotide in one or more phases of (usually separated) reaction materials, and especially in a liquid phase by virtue of displacement from the reagent complex and separation of displaced labeled polynucleotide in solution from probe polynucleotides and reagent complexes.

In the practice of the present invention, the probe polynucleotide can be a linear or circular polynucleotide capable of binding specifically through complementary base pairing in at least one region of its purine/pyrimidine base sequence to specific target nucleotide sequences of a sample. This binding may be between DNA and RNA, between DNA and DNA or between RNA and RNA. Accordingly, the probe may either be DNA or RNA. As discussed more fully below, it is generally only a specific region of the probe which binds selectively to the target nucleotide sequence. Other regions of the probe may be of various naturally occurring or synthesized sequences which do not participate in the hybridization reaction with the target nucleotide sequence, but which may play an important role in the present invention, e.g., by serving as a site for attachment to a support or by providing some degree of separation between the support and the region to which the target nucleotide sequence binds, if desired.

Referring to the region of the probe to which the target nucleotide will specifically bind, called herein the target binding region (TBR in the Figures), the binding region may be (and preferably is) perfect, in the sense that each nucleotide in the sequence finds its correct complementary binding partner (e.g., dA to dT) in the target nucleotide sequence or may contain some mismatches. At least one portion of the target binding region of the probe is preferably single-stranded in the reagent complex, i.e., it is not complementary to labeled polynucleotide sequences nor self-complementary; this single-stranded region is sometimes called herein the initial binding region (IBR in the Figures) because the target nucleotide sequence can bind to this region of bases without displacing any of the labeled polynucleotide. Such initial binding region of the probe is at least fifteen bases in length, and is preferably at least fifty bases in length. The overall target binding region includes the initial binding region and most or (preferably) all of the labeled polynucleotide binding region (LBR in the Figures and in the discussion below). The length of the overall target binding region is not independently critical, but rather can be considered as a function or sum of the preferred or more preferred lengths of the IBR and LBR portions. Base lengths of the initial binding region of the probe above five hundred are generally not required, but are not significantly disadvantageous in most cases. A suitable lower limit on the length of this region of base pairing for clinical laboratory applications is somewhat dependent upon base sequence of the target binding region of the probe polynucleotide and base composition and other physical factors described below, and especially upon the conditions for intended hybridization, mode of attachment, if any, of the probe to a support, kinetics of hybridization and the readout system employed.

The solid phase to or on which the probe can be immobilized in certain embodiments may be of almost any conventional type, including especially polymeric materials, ceramic materials, walls of a test tube or other container, paper, nitrocellulose or glass. In some forms of the invention, the solid phase consists of natural, modified natural or synthetic particles or beads made of materials such as protein, fixed cells or viruses various polymers such as polystyrene, latex or glass.

The means of attachment of the probe to the solid support in certain embodiments of the invention may be simple adsorption, but is preferably some form of specific covalent linkage, ionic bonding, hydrophobic interaction or hydrogen bonding. In the case of covalent linkage, the binding may be direct as by reaction between chemical moieties on the surface of the support (for example, amine or carboxyl moieties) and moieties on the polynucleotide, and especially hydroxyl or phosphate moieties on the end sugar rings of the polynucleotide. Linking agents which are specific to the free secondary hydroxyl normally present at the 3' end include phosphites, succinic anhydride and phthalamide. Linking agents which are specific to the phosphate normally present on the sugar at the 5' end (at least for most naturally occurring polynucleotides or products of most cleavage reactions) include carbodiimides such as 1-ethyl-3,3-dimethylaminopropylcarbodiimide, with or without imidazole or 1-methylimidazole. See B. C. F. Chu et al., *Nucleic Acids Research* Vol. 11, No. 8, pp. 6513-29 (1983). Such linkages which are specific to an end or other small portion of the probe, if remote from the target binding region, may permit greater degrees of freedom during the hybridization reaction compared to adsorption or other similar physical or non-specific chemical means of attachment. With such greater degrees of freedom, the minimum length of the target binding region or minimum time for the hybridization to progress to a detectable level may be lowered.

Non-specific covalent linkages include linkages between the substrate and free bases along the chain via moieties such as m-aminobenzyloxy methyl (ABM), m-diazobenzyloxy methyl (DBM) or o-aminophenylthioether (APT). See H. Bunemann et al., *Nucleic Acids Research* Vol. 10, No. 22, pp. 7163-7196 (1982) (two articles). Other exemplary non-specific linking chemistry is described in U.S. Pat. No. 4,286,964 to B. Seed (1981).

In addition to direct covalent linkage, the probe polynucleotide may be indirectly linked in a covalent fashion to the support by a linking or spacer molecule. Examples of indirect covalent linking reagents include spacer reagents which can react by carbodiimide chemistries both with functional groups (for example, esters) on the support and with the phosphate normally present on the 5' terminal sugar of the polynucleotide. Such spacer molecules include the aliphatic diamines used in the above-cited Chu et al. article which, once attached to the terminal phosphate, can then be linked to active groups on the support such as N-hydroxysuccinimide esters. Other spacer molecules include hydroxyalkanoic acids. Still other spacer molecules can also contain a functional moiety such as phenyl ketone which will react directly with a support having hydrazine moieties, forming a resultant hydrazone.

The probe further may be noncovalently linked to the support by interaction of some portion of the probe with affinity reagents that are adsorbed or covalently bound to the support. Examples include (1) immobilization on the support of a short single-stranded polynucleotide which can hybridize to some portion of the probe polynucleotide not overlapping with the region in the probe which is capable of binding to the target nucleotide sequence and (2) binding of a chemically modified probe polynucleotide carrying one or more avidin or biotin moieties to a support having biotin or avidin moieties, respectively, adsorbed or covalently bound to the support. The latter method is based on the high affinity ($K_{diss}$ approximately $10^{-15}M$) of the small molecule biotin for the protein avidin (or streptavidin).

While the present invention is not limited with regard to the spacings between the point or points of attachment of the probe to a support and the region of the probe polynucleotide which binds specifically to the target nucleotide sequence, it is preferable that this spacing be sufficiently large for the hybridization between target nucleotide sequence and target binding region of the probe polynucleotide to occur such that the target binding region of the probe has sufficient and preferably maximal obtainable freedom of movement during hybridization.

In other embodiments of the invention, the probe polynucleotide is not immobilized on a support, but rather the entire reagent complex is in solution as the reagent is mixed with a biological sample such that hybridization will occur, if at all, in solution. In some of those solution hybridization embodiments, the probe does contain a substituent (such as an affinity reagent, e.g., biotin, or a chemical moiety, e.g., a hapten such as dinitrophenol) so as to be immobilizable or separable if desired after hybridization, e.g., by passing through a porous bed or filter with strepavidin bound to a support matrix. Such immobilization will cause only displaced labeled polynucleotides to remain in the liquid phase, for subsequent determination. Still other forms of the invention involving solution hybridization include alternative methods of separations such as size exclusion chromatography (see Example 2, below), electrophoresis (see, e.g., Examples 1 and 3-7, below), or other physical separation techniques. Additional forms of the invention, described more fully below in connection with read-out, involve determination of displaced labeled polynucleotide without any separation from complex. Of course many of such determinations without separation apply equally to processes wherein the complex includes an immobilized probe polynucleotide.

Such probe polynucleotides can be manufactured reproducibly in a variety of ways, e.g., cloned in or as a part of a suitable plasmid or viral vector isolated from a bacterium or other suitable microorganism, as a part of the genetic material of a microbe or obtained from any other pertinent biological source. Generally, only a small region of nucleic acid that includes a probe polynucleotide sequence (a portion of which forms the target binding region) will be inserted into any such cloning vectors by recombinant techniques; the remainder, if any, of the cloned insert that is not probe polynucleotide sequence can conveniently be chosen from any polynucleotide sequence heterologous to the target nucleotide sequence. In certain embodiments of this invention, such heterologous sequences can include sequences deliberately selected for specific properties such as the presence of a unique restriction enzyme recognition site. Under some conditions an entire gene or a sequence including an entire gene may be used as an insert, with the vector plus inserted nucleotide sequence either in circular or linear form. In the event that the probe polynucleotide is double-stranded when manufactured, denaturation (either thermally, by adjustment of pH or by disruption of base pairing with other conventional techniques) will normally follow isolation. Cleavage (especially by restriction enzymes or by site-specific chemical cleavage) will normally be used to form double-stranded segments of desired linear form and, if double-stranded circular forms are grown, will precede denaturation. In some cases it may be preferred to purify individual strands from a double-stranded structure either to be used individually as probe polynucleotides or with one as a probe polynucleotide and the other as a precursor for the labeled polynucleotide. This purification can be done by standard techniques such as denaturing gel electrophoresis or affinity chromatography. In some instances, the probe polynucleotide is produced as a single-stranded molecule by replication using single-stranded vectors such as M13 bacteriophage. In some other instances, as described below, the labeled polynucleotide and labeled polynucleotide can be manufactured as parts of the same molecule.

The labeled polynucleotide used in the present method and reagent is generally a smaller piece of either DNA or RNA than the probe polynucleotide and has two features of significance: (a) stable but reversible binding to the probe at a specific locus and (b) a label susceptible to detection, especially after displacement. These features are discussed herein separately, followed by consideration of the effect certain types of labeling have on stability and displacement.

The pairing between the labeled polynucleotide and the probe polynucleotide will generally occur over a smaller number of bases than the pairing between the target nucleotide sequence and the probe. In most cases, the bases of the probe polynucleotide to which the labeled polynucleotide specifically binds are a subset of the bases of the probe later binding to the target nucleotide sequence of the sample, and thus represent a portion of what is called above the target binding region of the probe.

The term labeled polynucleotide binding region (LBR) is used herein to refer to that sequence of bases in the probe to which the labeled polynucleotide is bound in the complex. In preferred embodiments (as illustrated by all Figures) the labeled polynucleotide binding region is totally part of the target binding region (see especially FIG. 1A); in other embodiments (see FIG. 1G of parent application U.S. Ser. No. 607,885) only a portion (but preferably the major portion) of the labeled polynucleotide binding region is a part of the target binding region. Lengths of labeled polynucleotide binding region outside the target nucleotide binding region of the probe polynucleotide region that are greater than about 15 bases are not preferred because of the potential difficulty of disassociating the labeled polynucleotide from the probe once the only attachment is via base pairing in this region. In some of the preferred embodiments, the region of the probe polynucleotide to which the labeled polynucleotide binds is a subset at or near one end of the larger region of the probe polynucleotide to which the target nucleotide sequence of the sample subsequently binds. In some such embodiments, if the probe is immobilized in the reagent complex, the aforementioned one end of the larger region is at or near an end of a linear probe polynucleotide (as illustrated in FIG. 1A and discussed below; note, however, that the other end of the TBR may also be used as an LBR).

The present reference to a labeled polynucleotide and a probe polynucleotide as distinct entities should not be understood, however, to be a requirement that they are linked solely by complementary base-pairing or that there is necessarily only one labeled polynucleotide attached to each probe polynucleotide or that there is only one labeling moiety (tag) per labeled polynucleotide. Other forms of attachment of probe to labeled polynuclotide may also be present, but are generally not preferred. In embodiments without a separation, severing such other attachment of probe to labeled polynucleotide may or may not be required, depending upon whether or not displaced labeled polynucleotides still attached by such other means appear in the detection method as if they were totally displaced. Severing such other attachment before, during or after displacement but, in any event, before the determination step is preferred. Multiple labeled polynucleotides on a single probe strand (as illustrated in FIG. 6 of parent application U.S. Ser. No. 607,895) is a form of the invention which may have special application when greater numbers of displaced tags per displacement event are desired.

The size of the labeled polynucleotide binding region of the probe is not itself critical to the present invention, because wide variations in this size can be compensated for, e.g., by modifying the temperature of the displacement step (contacting step (b) described above) and by the size of the region of the probe to which the sample binds. A generally preferred size for labeled polynucleotide binding region (and the corresponding base sequence of the labeled polynucleotide) is at least about 15 bases, preferably at least 20 bases, and more preferably at least about 25 bases. A preferred range is about 20 to about 1000 bases (more preferably about 20 to about 500 bases, and most preferably about 25 to about 200 bases). Labeled polynucleotides with unusually short pairing segments (giving regard to factors such as GC base content) may dissociate from the probe in a non-specific manner if the temperature of the displacement step is too high (also giving consideration to factors such as salt concentration which affect melting temperatures). See D. Freifelder et al, *Biopolymers*, vol. 7, pp. 81-93 (1969). There is no essential advantage in unusually long pairing segments (e.g., over 1000 bases). Such long pairing segments are sometimes less preferred because the overall target binding region of the probe could then become longer and require necessarily longer target nucleotide sequences for successful displacement of the labeled polynucleotide. The binding portion of the labeled polynucleotide may, if too long, no longer easily be manufactured by certain techniques presently available or that are best suited for small polynucleotides: e.g., organic chemical synthesis of the entire labeled polynucleotide. Organic chemical synthesis is generally easier at present for labeled polynucleotide binding regions of less than about 100, and especially less than about 60; however, improvements in such synthetic techniques could make longer sequences easy to make as well.

The minimum length of labeled polynucleotide (and also of labeled polynucleotide binding region) is related primarily to reagent complex stability. Factors other than length which affect this stability include GC content (whose effect on melting temperature is well known) and internal base pair mismatches. Melting temperature is a useful way to establish an effective length for sequences having one or more internal base pair mismatches. As an example, a sequence of 30 bases having one internal base pair mismatch (and thus only 29 exact pairs) may perform (at least with regard to reagent complex stability) effectively like a shorter exactly matched sequence; the degree of departure from behavior as a 29 base pair sequence will depend upon the position of any base pair mismatches and the base change that has been made. Effective length can be expected to differ depending upon whether the mismatched pair is purine/purine, purine/pyrimidine or pyrimidine/pyrimidine. Any effective length can be empirically determined, however, by melting temperature experiments in which a series of probe/labeled polynucleotide complexes are subjected to various temperature regimes as illustrated in Example 8 of parent application U.S. Ser. No. 607,885, and in articles such as R. L. Ornstein and J. R. Fresco, *Biopolymers*, vol. 22, pp. 1979-2000 (1983). By determining a melting temperature of a complex of probe with a labeled polynucleotide containing base pair mismatches, and comparing that value with melting temperatures of complexes with slightly shorter lengths of pairing (but perfect base pair matching within the paired region) on the same probe polynucleotide, the effective pairing length of the labeled polynucleotide with base pair mismatches can be estimated and applied to the above preferred and more preferred ranges. The above correlations based upon melting points are intended, however, primarily as an easy estimation tool. The actual degree of preference for a given labeled polynucleotide binding region is based both on how well the labeled polynucleotide actually stays in the complex during storage of the reagent or contact with non-homologous nucleic acids under use conditions and on how well the labeled polynucleotide is displaced by nucleic acids having the appropriate target nucleotide sequence. While base pair mismatches are permitted, they are in general not preferred and, when present, generally comprise no more than two fifths and preferably comprise no more than one tenth of the region of pairing (e.g., a preferably maximum of three mismatches and twenty-seven perfect matches in a 30 base pair long region of labeled polynucleotide/probe polynucleotide pairing).

The labeled polynucleotide may contain regions of nucleotides, in addition to the pairing region, which do not specifically bind to the probe polynucleotide. Such regions may serve to link the pairing region to the detectable tag, may themselves be tagged (e.g., by radioactive labeling or by covalent attachment to an indirect marker such as avidin or biotin) or merely be present without any particular function. The labeled polynucleotide may itself be linear or circular and may be (but is preferably not) double stranded in regions other than the pairing region. The labeled polynucleotide is preferably not circular when the probe polynucleotide is circular because of possible topological constraints on hybridization of two circular nucleic acid molecules and possible constraints on hybridization with the target nucleotide sequence.

One or more detectable tags may be generally located (using conventional techniques) at one or more of several points along the labeled polynucleotide (especially if the tag is a radionuclide or biotin or the like), only at one end or only at one specific internal location on the labeled polynucleotide (e.g., at a purine or pyrimidine base not involved in base pairing to the probe polynucleotide). Provided that there is at least one region of the labeled polynucleotide unpaired in the reagent complex, the tag is preferably present or concentrated on or within such unpaired region. Directly detectable tags which may be used include radionuclides (especially phosphorus-32, sulfur-35, carbon-14 or iodine-125 labeled nucleotides), fluorescent compounds (such as fluorescein or rhodamine derivatives attached to the free end of a labeled polynucleotide or to one or more of the unpaired bases of a labeled polynucleotide) or moieties directly detectable by other means (including being cleaved off) such as the moiety nitrophenol detectable colorimetrically or otherwise. Indirectly detectable tags include those modifications that can serve as antigenic determinants, affinity ligands, antigens or antibodies recognizable through immunochemical or other affinity reactions such as described in EPA No. 63,879, WO No. 83/02277 and EPA No. 97,373, referenced above and exemplified by biotinated nucleotides present in or added onto the labeled polynucleotide (such as by the enzyme terminal deoxynucleotidyl transferase which will add multiple nucleotides at the 3' end of the labeled polynucleotide in the absence of a template strand). Other indirect tags include enzymes attached to a labeled polynucleotide (especially at a free end remote from the region paired to the probe) whose presence can be determined after displacement and separation steps of the embodied method by addition of the substrate for the enzyme and quantification of either the enzymatic substrate or, preferably, the enzymatic reaction product. Similarly, the tag may be an apoenzyme, co-enzyme, enzymatic modifier, enzymatic cofactors or the like, with the other necessary reagents usually added after displacement (and, in certain embodiments, separation) along with the appropriate enzymatic substrate, after displacement (and, in certain embodiments, separation). Of course, if the enzymatic reaction cannot occur with all but one component present (e.g., the substrate), then these other reagents may be present in solution during the contacting (displacement) step (b) described above.

Multiple detectable tags can be added in manufacturing the labeled polynucleotide such as by using a terminal deoxynucleotidyl transferase enzyme. Multiple labeled polynucleotides, e.g., one containing the enzyme (or apoenzyme) and one containing the coenzyme, can also be used. One form of attachment of an enzyme to the labeled polynucleotide is via affinity reagents, e.g., streptavidin to biotin. Such a binding form can be used in various embodiments, for example wherein the complex is prepared by hybridizing a biotin-labeled polynucleotide to the probe and then binding a streptavidin-enzyme conjugate to the biotin prior to the contacting (displacement) step (b), described above. Furthermore, a moiety interacting with the detectable tag in the complex may be present on the probe.

Most forms of detectable tags, especially if remote from the pairing region of the labeled polynucleotide to the probe, will have little or no effect on the strength of base pairing between the labeled polynucleotide and the probe polynucleotide, as evidenced (for testing purposes) by little or no diminution of the reagent complex melting temperature and, more importantly, by negligible effects on the hybridization reaction between any target nucleotide sequence and the probe polynucleotide Some forms of labeling, such as covalently bound biotin on nucleotides of the labeled polynucleotide in the base pairing region and such as a large enzyme molecule or fluorescent moiety linked to nucleotides in or near the pairing region, may have an appreciable effect on reagent complex stability. Such effect generally will be to destabilize the labeled polynucleotide/probe polynucleotide binding (and thus lower its melting temperature). That effect may be somewhat beneficial in speeding up displacement, but can cause increases in non-specific dissociation or "fall-off" of the labeled polynucleotide. Such non-specific "fall-off" can usually be reduced, however, by lowering the temperature during the displacement step, increasing the length of the labeled polynucleotide binding region, or other such modification of the physiochemical properties of the system.

Forming a reagent complex between an immobilized probe polynucleotide and a labeled polynucleotide (such complex being provided in the present process and being in the present reagent) may involve attachment of the probe to a support (as described above) either before or after hybridization of the labeled polynucleotide to the probe polynucleotide. Affinity or other chemical reagents may be used for mediating or participating in such attachment. If the immobilization is completed after hybridization of the labeled polynucleotide to the probe polynucleotide, then the linking moiety or a part thereof can be already attached to the probe. Generally, the formation of such an immobilized complex will be followed by washing off unbound labeled nucleotide, and the conditions of such washing may be designed to also remove labeled polynucleotides that are only slightly bound (e.g. through less than about fifteen complementary bases elsewhere on the probe, instead of through the larger number of complementary bases at the desired binding site) or are adsorbed to the support. Probe polynucleotides and complexes of probe polynucleotide with labeled polynucleotide that are only marginally attached to the support may also be removed during this washing step. The washing should preferably be under sufficient conditions and for a sufficient time to substantially eliminate the non-specific background signal due to labeled polynucleotides (with or without probe polynucleotide) separating from the support independently of specific displacement during the displacement step of the present method. One can also use a reagent (e.g., protein) to block any non-specific binding sites on the support.

In the manufacture of reagent complexes which are in solution when used, it is frequently also desirable to separate labeled polynucleotides which have not bound to probe polynucleotides from product reagent complexes (in some instances unbound probe polynucleotides may also be removed). Such separation may be by size alone (e.g., by size exclusion chromatography) if, as is frequently the case, the labeled polynucleotide is much smaller than either probe polynucleotides or reagent complexes. Such separation may also be based upon the double-stranded nature of at least one portion of the reagent complex (at the labeled polynucleotide binding region of the probe) where such a double-stranded region is not likely to be present in either the labeled polynucleotide or probe polynucleotide, both of which would be expected to be in single-stranded form except for very small internal binding regions. This property renders reagent complexes separable from unbound labeled polynucleotides by, e.g., affinity chromatography using double-strand specific anti-nucleic acid antibodies or hydroxylapatite chromatography.

In some instances, the labeled polynucleotide and probe polynucleotide can be part of the same polynucleotide chain. For example, a linear single-stranded DNA molecule can be constructed from an M13 bacteriophage which contains a cloned DNA insert with inverted repeats. These inverted repeats, which are capable of forming a double-stranded region due to their complementarity, would include the labeled polynucleotide and the labeled polynucleotide binding region. Sequences located between or adjacent to these repeats would include the initial binding region, located adjacent to the labeled polynucleotide binding region. Unique restriction enzyme cleavage sites, e.g., the M13mp7 polylinkers or modifications thereof, located outside of the inverted repeats and the initial binding region, could be cleaved to release the cloned insert from the single-stranded M13 vector backbone (c.f. G. A. Ricca, J. M. Taylor & J. E. Kalinyak, *Proc. Nat. Acad. Sci. U.S.A.*, vol. 79, pp. 724–728 (1982). An additional small inverted repeat sequence, containing a restriction enzyme cleavage site (e.g., the M13mp7 polylinker) could be placed between the labeled polynucleotide repeats. Cleavage at such a site (e.g., X of FIG. 3D of parent application U.S. Ser. No. 607,885) would leave only complementary purine/pyrimidine base pairing to hold the labeled polynucleotide attached to the now distinct probe polynucleotide and would provide free ends on the probe polynucleotide through which attachment to a solid support could be mediated if so desired. Any tag or tags may be added to the labeled polynucleotide at this point if not already present.

If a polyether, the volume-excluding polymer used in the present invention may be a simple poly(alkylene oxide) such as those of the formula $H(O-R)_n-H$ where R is alkylene of 1–6 carbons and n is an integer (on a weight average basis) of 15–1000. R can be methylene, 1,1-ethylene, 1,2-ethylene, 1,2-propylene 1,4-butylene, 1,2-butylene, 1,2-hexene (2-butylethene) or similar divalent saturated hydrocarbon moieties, and can be mixed within a single molecule. Preferably R is 1,2-ethylene or 1,2-propylene as in poly(ethylene glycol) (PEG, also called poly(ethylene oxide) or PEO) or as in poly(propylene glycol) (PPG, also called poly(propylene oxide) or PPO). The integer n in such instances represents the weight average molecular weight divided by the monomeric unit molecular weight; such molecular weight for PEG is 44 and for PPG is 56. For PEG, weight average molecular weights are preferred empirically to be at least about 1500, preferably at least about 2500 and more preferably between about 3000 and about 20,000. Accordingly, n (on a weight average basis) is preferably at least 36, more preferably at least 60 and most preferably between about 70 and about 690. A similar set of preferred ranges for n in PPG is expected.

Also included as suitable polyether polymeric agents are condensation products of ethylene oxide, propylene oxide or other alkylene oxides on various moieties such as diols, triols, sugars or acids. Such materials are well known in the art of non-ionic detergents and may be effective in the present invention provided that the molecular weight (and water solubility) is sufficient to enhance displacement without unduly enhancing non-specific dissociation of labeled polynucleotide from the probe polynucleotide.

In the broader forms of the invention, however, other chemically inert, water-soluble nonionic or anionic polymers may be used as the volume excluding polymer in place of or in conjunction with the above polyethers. Examples include polyacrylates, poly(vinyl acrylates), derivatized and underivatized polysaccharides, polyphosphoric acid, various copolymers containing pendant carboxyl, sulfonate, sulfate, phosphate, or other anionic moities. A material shown in Example 10, below, to have limited beneficial effects is FICOLL, MW 400,000 (a cross-linked reaction product of sucrose with epichlorohydrin having free hydroxyls; FICOLL is Pharmacia's trademark). A class of suitable non-ionic volume excluding polymers are thus the reaction products of a sugar with epichlorohydrin.

Certain volume excluding polymers are preferably used in the total method of the invention, involving both the contacting (displacement) step and the determining (detecting) step only in forms in which their beneficial effects upon the displacement reaction are not outweighed by deleterious effects upon the determination step or a portion of the determination step. For example, in those embodiments wherein the determination step includes a separation (e.g., gel chromatography, size exclusion chromatography, affinity chromatography or electrophoresis), the presence of certain volume excluding polymers may have deleterious effects. Dextran sulfate, while believed to be useful in promoting displacement, was observed in several experiments to have deleterious effects upon electrophoresis (under the particular conditions tested) and in more limited experiments to have deleterious effects upon size exclusion chromatography (under the particular conditions tested). It is believed, however, that one can find, through routine experimentation, suitable polymers for any particular embodiment of the present method and can find, through routine experimentation, suitable detecting or determining conditions for using any polymer which has the effect of promoting the hybridization and displacement process.

The actual contacting or displacement step with sample material (potentially containing nucleic acids that may include the target nucleotide sequence) will normally be under conditions of temperature, ionic strength, polyether polymer concentration and time less stringent (and thus less conducive to non-specific uncoupling of the labeled polynucleotide) than the above washing step. A desirable temperature range during the contacting step is from about 15° C. to about 90° C., depending upon the solution ionic strength and other additives affecting melting temperature; the most efficient temperature will be one at which a maximum or near maximum rate of hybridization of sample nucleic acids to probe occurs. In certain cases, however, a more convenient (generally lower) temperature such as from near ambient temperature (15°–25° C.) up to physiological temperatures (37°–40° C.) may be used. As described in a number of literature references (e.g., J. G. Wetmur and N. Davidson, *J. Mol. Biol.*, vol. 31, pp. 349–370 (1968) and C. Minson and G. Darby, *New Developments In Practical Virology*, vol. 1, p. 185–229 (Alan Liss, Inc., N.Y., 1982)), hybridization rate is also a function of pH and sample nucleotide concentration. Also, in addition to the application of a polyether polymer in the preferred assay methods described herein, other water soluble volume excluding polymers such as dextran sulfate can be used in conjunction with the polyether polymer. Enzymes and other proteins which affect the displacement process (such as the *E. coli* ATP-dependent rec A protein) may further be present, however, based upon their beneficial effects described in our copending, commonly assigned application Ser. No. 684,305, filed herewith.

Proportions, amounts and concentrations of reagent complex and polyether polymer are not independently critical, but it is generally desired that the total hybridization mixture of sample and reagent complex be as concentrated as feasible. In most instances, probe polynucleotides bearing binding sites for the target nucleotide sequence will be expected to be present in ten-fold or more molar excess (possibly hundred-fold or more molar excess) of any anticipated level of target nucleotide sequence in the sample. The sample itself may include nucleic acids which preferably should be completely or partly in solution (separated from membranes and the like) and in single-stranded form for the hybridization step of the assay. The presence of the unlabeled complement of the target nucleotide sequence (by virtue of denaturation of double-stranded sample DNA) could represent an interference. This interference is likely to be minor in at least the preferred forms of the invention due to the usual molar excess of reagent over sample strands having the target nucleotide sequence or its complement; in hybridizations involving immobilization of the probe selectively (before or after displacement), displaced labeled polynucleotide will be and will remain in the solution phase and be subsequently determined, whether or not such displaced labeled polynucleotide has rehybridized with complementary segments of the sample nucleic acid. In many solution hybridizations this interference may also be minimized by kinetic effects.

In general, the optimal proportions of polyether polymer can be expressed as a weight proportion (weight-/vol or weight %) of the total aqueous phase during the displacement reaction. Such proportion will generally be from 2% up to the solubility limits of the polyether polymer and will preferably be between about 5% and about 20% (weight %). For particular reagent complex and displacement conditions, optimal proportions and appropriate polymer molecular weight can be further determined by routine experimentation as illustrated in Examples 4 and 5.

The basis for the volume exclusion phenomenon, incompatability of two water soluble polymers (in the present case being the nucleic acid and the volume excluding non-ionic or anionic polymer), is summarized in P. Molyneux, *Water-soluble Synthetic Polymers: Properties And Behavior*, Vol. 2, pp 167–170 (1984) (see also references cited therein).

In general, displacement reactions using volume excluding polymers should require no more than three hours, generally under one hour and desirably less than thirty minutes to occur to a sufficient extent for detection. Conditions often can be adjusted to achieve substantial completion of strand displacement reactions within these times. Longer incubation times are not necessarily disadvantageous, however. It is believed that the rate-limiting step is a sample or target nucleotide sequence finding a complementary sequence of the probe polynucleotide (cf. C. Green and C. Tibbetts, *Nucleic Acids Research*, vol. 9, pp. 1905–18 (1981)); once target/probe hybridization begins to occur, displacement of labeled polynucleotide is expected to occur from each individual reagent complex in under one minute and frequently less than one second.

In some of the forms of the invention in which the complex is initially on a solid support, the liquid phase containing displaced labeled polynucleotide may be separated therefrom as a part of the determination step. If the complex is in solution, some forms of the invention involve treatments after the contacting (displacement) step to fix reagent complexes still present (and, unavoidably, in some cases other forms of the probe including those hybridized to a target nucleotide sequence) to a solid support, followed by a similar solid/liquid separation. Such separation of the solid phase containing bound complex from liquid phase containing displaced labeled polynucleotide may be by physical means such as chromatography, filtration, centrifugation, magnetic attraction or decantation. The solid phase may include magnetic or other separable particles that are attracted or otherwise physically removable from the liquid phase. Furthermore, complete separation of the two phases is not required; an aliquot of the liquid phase following partial separation may be removed for label determination, leaving the solid phase admixed with the remainder of the liquid phase. If such a separation occurs or is used, determination (detecting) of the presence and frequently the quantity of labeled polynucleotide present may be conducted upon either phase, but is preferably conducted upon the liquid phase. Determination of the label in the liquid phase as a measure of the presence and quantity of displaced labeled polynucleotide typically has the advantage of generally lower background signals. Any background signal will be largely that caused by non-specific fall-off from a solid support as described above, by non-specific dissociation of labeled polynucleotide strands from reagent complexes, or by imperfect preparation of reagents. Additionally, the absence of target nucleotide sequence in the sample results in the proportional absence of signal above background levels from labeled polynucleotide in the liquid phase. By contrast, if detection is of the label associated with the solid phase, a negative result is indicated by unreduced levels of labeled polynucleotide. Especially when a high molar excess of reagent complex over sample nucleotide sequences over anticipated target nucleotide sequences is used, measurement of the label remaining on the solid support results in substantially reduced sensitivity.

In some embodiments of the invention, no post-displacement separation occurs, and determination can still be made of displaced labeled polynucleotides. Some such determination (detecting) steps involve a change in the signal detectable from a tag by virtue of displacement, including those signals affected by proximity of the tag to a signal-affecting moiety elsewhere on the labeled polynucleotide or on the probe polynucleotide (see description of FIG. 3A-3D of patent application U.S. Ser. No. 607,885).

In other forms, especially with immobilized probes, the interaction can be between two types of tag moieties. One type of detectable tag can be on labeled polynucleotides hybridized to immobilized probe polynucleotides at one location on a solid support. A second type of tag may be on labeled polynucleotides which are hybridized to immobilized probe polynucleotides at a remote location on the same solid support or on a separate solid support in close physical proximity. The second type of tag may also be otherwise directly attached to some remote location of the probe or of the same labeled polynucleotide or of the solid support. In all such cases involving two types of tags, the two different tags can interact only if at least one labeled polynucleotide (tag) is displaced. Such interaction is especially applicable to apoenzyme with coenzyme: e.g., apoglucose oxidase with flavin adenine dinucleotide (FAD).

The process and reagent of the present invention can be used for the detection and determination of a variety of target nucleotide sequences in a variety of concentrations. In particular, microorganisms including infectious agents whose nucleic acid (genomic or otherwise) can be targeted include pathogenic viruses, bacteria and fungi; e.g., cytomegalovirus or *Neisseria gonorrhea*. Exemplary genetic disorders or conditions which can be targeted include $\beta$-thalassemias, $\alpha_1$-thalassemias, cri du chat syndrome and some retinoblastomas. The present process and reagents are applicable to detecting genetic disorders or variations primarily when a multi-base nucleotide deletion, insertion, substitution or transposition is involved in distinguishing the target nucleotide sequence from the closest sequence present in samples intended to be read as negative for the target sequence. To the extent that the present invention is applicable to genetic disorders due to single base mutations, if at all, the complement of the substituted base or other point of mutation is desirably part of the target binding region of the probe polynucleotide, with the location of that base within the region likely to affect the selectivity of the method. Changes or differences in the expression, activation or rearrangement of structural genes, regulatory genes or oncogenes can be detected by the present method. For monitoring gene expression, mRNA would be targeted. Other perturbations in the expression of structural genes can be similarly detected. The present process can also be applied to histocompatability typing for tissue transplantation, determination of antibody resistance genes in microorganisms, and to the screening of food, medicinal and water samples for specific infectious agents or other microorganisms.

Selecting a target sequence for a particular test involves determining a sequence which is unique or relatively unique to the target organism or condition. Such target sequence would be used to develop the target binding region (which is complementary thereto) and then a labeled polynucleotide of appropriate length would be developed to bind to a part of the target binding region. In some instances multiple reagent complexes targeting different parts of the nucleic acid of the same organism or condition may be used in order to impart improved specificity when any particular target sequence is only relatively unique.

One embodiment of the present invention is illustrated, for purposes of understanding, by reference to attached FIGS. 1A-1E, in which is shown an immobilized probe polynucleotide P, 3300 nucleotides in length. Numbering from the 5' end, the region from nucleotide 3000 to nucleotide 3300 represents the target nucleotide binding region (TBR). For simplicity, it is assumed that the first nucleotide of the probe is directly attached to a support S. As illustrated in FIG. 1A, the labeled polynucleotide L consists of 150 bases to which a tag T is attached at the 5' end. Of these 150 bases, 51 (from base number 100 to base number 150) bind specifically to the labeled polynucleotide binding region (LBR), bases 3250 to 3300, of the probe. Accordingly, when the immobilized probe consisting of probe polynucleotide P attached to support S is incubated with a solution of labeled polynucleotide L under normal hybridization conditions, a complex will be formed as shown in FIG. 1A with labeled polynucleotide L attached at the end of the probe polynucleotide P via base pairing between bases 3250–3300 of the probe P and bases 100–150 of the labeled polynucleotide L.

Figure 1B:
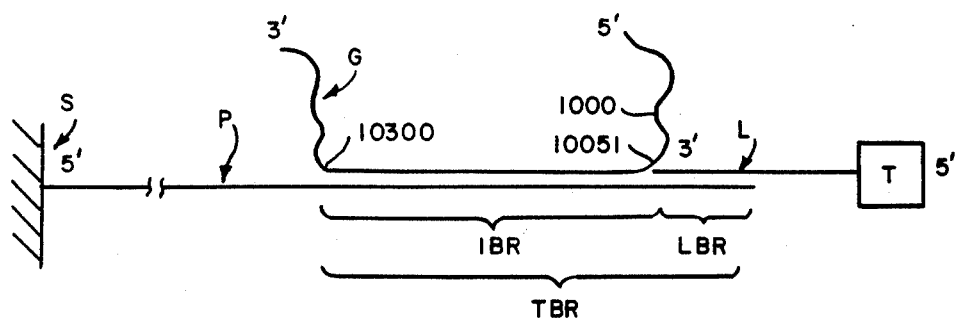
FIG. 1B is a view similar to FIG. 1A, in which the reagent complex is partially hybridized with a target nucleotide sequence G of sample nucleic acid.
Figure 1C:
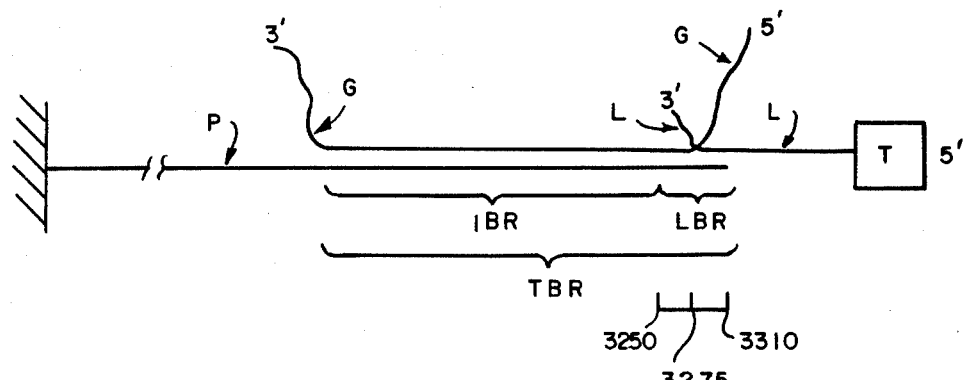
FIG. 1C is a view, similar to FIG. 1B, in which the target nucleotide sequence of the sample nucleic acid has begun to displace labeled polynucleotide from the reagent complex.
Figure 1E:
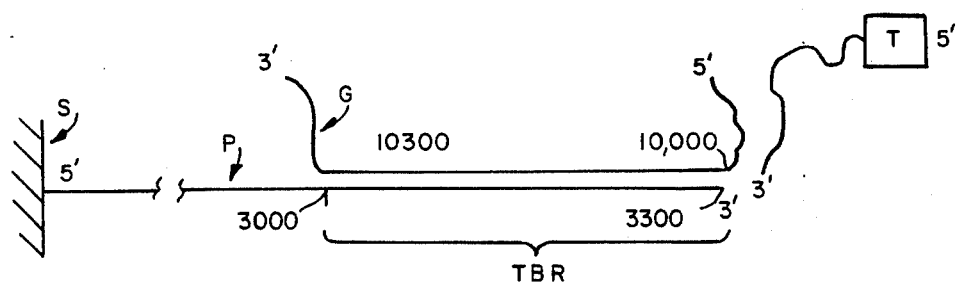
FIG. 1E is a view, similar to FIG. 1C, in which the labeled polynucleotide has been fully displaced from the reagent complex.

In use, the illustrative complex is contacted with a biological sample under hybridization conditions where the sample contains a nucleotide sequence with bases 10000 to 10300 of this sequence which corresponds to and binds selectively to the target binding region TBR of the probe. Under proper hybridization conditions, the sample polynucleotide G would first bind, as illustrated in Fig. 1B, from base 10051 to base 10300 of G and base 3000 to base 3249 (the initial binding region or IBR) of probe P. The IBR in the reagent complex shown in FIG. 1A is entirely single stranded. It should be appreciated that thermodynamic considerations favor the formation of double-stranded moieties such as shown in FIG. 1B over single-stranded moieties. It is believed, however, that this initial hybridization is the rate-limiting step and that the present use of volume excluding polymers facilitates or speeds up this step under many conditions. Thereafter, an equilibrium is created at bases 3250 to 3300 (LBR) of the probe polynucleotide P between binding to the labeled polynucleotide L and binding to bases 10000 to 10050 of the sample polynucleotide G. Under these conditions, a rapid zippering and unzippering will occur, as represented by the differences between FIG. 1B on the one hand and FIG. 1C on the other hand, along with random migration of the branch point along the probe polynucleotide. In such event, when additional bases of the sample polynucleotide G bind to the probe polynucleotide beyond probe base 3249, corresponding bases of the labeled polynucleotide L are displaced, creating a free end. Under the conditions described herein, this zippering and unzippering can occur in either direction; but the favored event will be eventual shifting of the point of attachment to the right in FIG. 1C. FIG. 1D shows the stage of near total labeled polynucleotide strand displacement in somewhat enlarged and more graphic form from base number 3275 on the probe P toward base number 3300, at which point the labeled polynucleotide L is totally displaced from the probe P (cf. FIG. 1E). It should be appreciated that, merely upon random zippering and unzippering in both directions, removal of the labelled polynucleotide L will be favored in that FIG. 1B represents the furthest to the left that the labeled polynucleotide L can displace the target nucleotide sequence of sample polynucleotide G. As long as some substantial region of the initial binding region IBR exists in which a sequence of nucleotides of the probe polynucleotide P binds selectively to the target nucleotide sequence, but not to the labeled polynucleotide, displacement of the sample polynucleotide G completely from the probe will be a rare and reversible event.

An important parameter in optimizing the present method and reagent is the length and nature of the base pairing between the labeled polynucleotide and the probe polynucleotide. As compared to the 51 bases of exact pairing illustrated in FIG. 1A, modification may be made either by shortening or increasing this length, by introducing mismatches or loops in either strand or by selecting between DNA and RNA for either or both strands so as to affect the rate of spontaneous (and presumably also specific) dissociation. In this regard, certain differences can be achieved when the target nucleotide sequence is RNA and the labeled polynucleotide is DNA, whether the probe polynucleotide P is either DNA or RNA. This is because, in general, RNA-RNA binding is strongest per base pair, DNA-RNA base pairing is of intermediate strength and DNA-DNA base pairing is of the least strength per base pair. If, however, the target binding region (TBR) is larger than the labeled polynucleotide binding region (LBR), then the labeled polynucleotide can be RNA and still be displaced by a DNA target nucleotide sequence. Targeting RNA may be required if, for example, the target microorganism is an RNA virus or the target condition is one of altered gene expression.

One means of reducing the binding strength in the region in which the labeled polynucleotide is bound to the probe polynucleotide is the introduction of individual base mismatches into the labeled polynucleotide. Assuming that the probe nucleotide sequence will be chosen to pair exactly or nearly exactly to the target nucleotide sequence, such mismatches can be considered as mutations or individual base substitutions in the labeled polynucleotide compared to a similar polynucleotide segment of the target nucleotide sequence which has exact (or nearly exact) binding. Such mutation or substitution may include the substitution of a natural or chemically modified nucleotide for a given natural nucleotide such as the following: G for A (to produce the apposite pair dG-rU, dG-dT, rG-dT or rG-rU), A for G, 5-methylcytosine for C, 5-hydroxymethylcytosine for C, gentibiosyl-5-hydroxymethylcytosine for C, or 5-bromouracil for A. In many preferred embodiments, such mutations involve the substitution of one naturally occurring nucleotide for another nucleotide. In certain such embodiments, the substitution involves the substitution of a pyrimidine for a purine, leading to a mismatched pair that has become a pyrimidine-pyrimidine pair. Because pyrimidines occupy less space than purines, such individual pyrimidine-pyrimidine mismatches can have a minimal effect upon adjacent nucleotide pairings. Purine-pyrimidine mispairings (for example, A being positioned opposite to C, or T or U being positioned opposite to G) are somewhat more space filling, but are still generally less space filling than the positioning of two purines (A-A, A-G or G-G) apposite each other. Counteracting the space-filling effect, however, is a stacking energy effect which runs in the opposite direction: generally, purine/purine base pairs display a lower free energy of stacking, purine/pyrimidine base pairs somewhat more and pyrimidine/pyrimidine base pairs somewhat more still. See R. L. Ornstein & J. R. Fresco, *Biopolymers*, Vol. 22, pp. 1979–2016 (1983) (two articles). The net effect, in terms of effect on melting temperature of the reagent complex, in terms of effect on stability of the reagent complex and in terms of effect on the displacement kinetics, will primarily represent a combination of these two counteracting effects, such that experimentation may be required to determine which, if any, mismatches may be preferably incorporated into the labeled polynucleotide for a particular probe after the position of the target nucleotide region and labeled polynucleotide region are fixed.

In addition to point substitutions, mismatches can be created either by inserting a short sequence in the labeled polynucleotide L which does not correspond to the probe nucleotide sequence (e.g., inserting a series of A's between bases 125 and 126 of labeled polynucleotide L in the example illustrated in FIG. 1A) or by deleting a portion (such as by deleting bases 120–130 of labeled polynucleotide L in FIG. 1A). Insertions in the labeled polynucleotide will generally form a single-stranded loop or cruciform structure of the labeled polynucleotide; deletions therein will generally form a single-stranded loop or cruciform structure of the probe polynucleotide.

Such substitutions, deletions or insertions will have the effect of destabilizing the binding between the labeled polynucleotide L and the probe polynucleotide P such that the displacement of the labeled polynucleotide may be increasingly favored. It is important, however, to avoid to the extent possible nonspecific displacement of the labeled polynucleotide L from the probe polynucleotide P in the absence of the target nucleotide sequence. The minimum length of binding between the labeled polynucleotide L and the probe polynucleotide P which is sufficient to minimize such dissociation or falling off will be dependent on a number of factors including, especially, the conditions such as pH and temperature of hybridization, the mode of attachment of the probe polynucleotide to the support (e.g., end attachment versus nonspecific adsorption), the extent of destabilizing substitutions (or deletions or additions), the duplex base sequence at the region of hydrogen bonding and whether the binding is between RNA and RNA, DNA and RNA or DNA and DNA. The optimal conditions in a particular instance can be determined empirically with routine experimentation based upon the general teachings of the present disclosure. Such experimentation may involve melting temperature experiments with samples lacking the target nucleotide sequence for purposes of estimating stabilities, and then displacement experiments for final optimization.

In considering the geometric relationship between the region where the labeled polynucleotide binds to the probe polynucleotide (LBR) and the region where the target nucleotide sequence binds to the probe polynucleotide (TBR) a configuration such as that illustrated in FIGS. 1A–1B may be used, with the labeled polynucleotide binding region being a subset of and at the end of the target binding region distal to the solid support. A common end of the TBR and the LBR (probe nucleotide 3300 in FIG. 1A) may also be (or be near to) one end of the probe polynucleotide. There are, however, no great disadvantages in having the probe polynucleotide extend beyond this point in a sequence of a nonspecific nature. There may be situations in which it is desirable to have a probe polynucleotide continue beyond this pairing region and extend to a point of attachment of a tag (different from the tag T on labeled polynucleotide L) which is to be released subsequently by other techniques. Furthermore, the two tags (one on the labeled polynucleotide, the other in the probe polynucleotide) may interact, with the interaction being detected as a part of the read-out. It may be preferred in certain embodiments of the invention that the labeled binding region be near or at the end of the target binding region nearest the support.

Various other geometries suitable for practice of the present method, either by a displacement reaction from a supported probe or by a displacement reaction in solution, are illustrated in FIGS. 1F, 1G, 2, 3A, 3B, 3C, 3D, 4, 5 and 6 and the accompanying description in parent application U.S. Ser. No. 607,885 (incorporated herein by reference).

EXAMPLES

In the following Examples 1–7, a synthetic oligomer of 27 nucleotides (Table 1) was used as the labeled polynucleotide; in all instances it was labeled with radioactive phosphorus-32 ($^{32}P$) at its 5'-end (A. M. Maxam et al., Proc. Natl. Acad. Sci. U.S.A., vol. 74, pp. 560–564 (1977)). The oligomer is a perfectly matched complement to 27 bases at the BamHI end of a 1.1 kb PstI-BamHI restriction fragment from pBR322. This 1.1lkb restriction fragment was cloned in opposite orientations by standard procedures into bacteriophages M13mp8 and M13mp9, generating clones designated M13mp8 clone 20 and M13mp9 clone II-16 which have pBR322 DNA inserts that are complementary to one another. The plus strand of M13mp9 clone II-16, hereafter referred to as probe DNA, harbors the sequence complementary to the 27-mer at the 3' end of the pBR322 insert. The plus strand of M13mp8 clone 20, occasionally referred to herein as competitor DNA, contains the complement of the pBR322 sequence present in the probe DNA and is thus homologous for 27 bases near one end of the DNA insert to the synthetic oligomer.

TABLE 1

| Nuleotide Position: | 350 |
|---|---|
| Probe: | 5'... —T—A—C—G—C—G—A—T—C—A— |
| Oligomer | 3'C—T—A—G—T— |
| Position: | 360 |
| Probe: | T—G—G—C—G—A—C—C—A—C—A—C—C—C— |
| Oligomer: | A—C—C—G—C—T—G—G—T—G—T—G—G—G— |
| Position: | 370           380 |
| Probe: | G—T—C—C—T—G—T—G—G—A—T— ... 3' |
| Oligomer: | C—A—G—G—A—C—A—C  5' |

EXAMPLE 1

Hybrids between M13mp9 clone II-16 DNA and the radiolabeled 27 base oligomer were prepared by heating 0.4 pmole M13mp9 clone II-16 DNA plus 2.0 pmole oligomer in 36 μl 5X SSC (1X SSC=0.15M NaCl, 0.015M sodium citrate) at 65° C. for five minutes, then 50° C. for 30 minutes. The solution was fractionated over a 5.0 ml Sepharose ® 4B column in 10mM Tris-HCl, pH 8.1, 1.0 mM $Na_2EDTA$ and radioactivity for each fraction determined by Cerenkov radiation counting. The hybrid (reagent complex) fractions were pooled. The elution profile indicated that more than 45% of the probe strands (M13mp9 clone II-16 DNA) were hybridized to oligomer (1100 cpm per 10 μl). Approximately 10 ng of reagent complex were incubated for 0, 30, 60, 90, 120 or 150 minutes in 20 μl 2X SSC or 5X SSC at 50° C. prior to analysis by gel electrophoresis on 15% polyacrylamide slab gels and autoradiography. The results from the autoradiograms showed that there is no spontaneous dissociation of the reagent complex at this temperature ($T_m-18°$) for at least 150 minutes under conditions which mimic those for competitive strand displacement.

Samples of reagent complex (50 ng) were subsequently mixed with 0% or 8% PEG (MW 6000) in 24 μl 5X SSC and either no competitor DNA or 50 ng of competitor M13mp8 clone 20 DNA and incubated at 50° C. for 0, 30, 60 or 90 minutes before analysis by gel electrophoresis in 15% polyacrylamide slab gels. Densitometric scans of the resulting autoradiograms show that strand displacement was barely detectable in the absence of PEG, but significant in the presence of 8% PEG even at the earliest observation time (Table 2). PEG therefore has a significant and specific effect on the rate of strand displacement at this concentration.

TABLE 2

| Minutes of Incubation | 8% PEG (MW 6000) | 50 ng Competitor DNA | Percent Free Oligomer |
|---|---|---|---|
| 0 | − | − | 26 |
|   | − | + | 21 |
|   | + | − | 23 |
|   | + | + | 25 |
| 30 | − | + | 28 |
|   | − | + | 29 |
|   | + | + | 77 |
|   | + | + | 79 |
| 60 | − | + | 19 |
|   | − | + | 24 |
|   | + | + | 94 |
|   | + | + | 99 |
| 90 | − | − | 26 |
|   | − | + | 33 |
|   | + | − | 19 |
|   | + | + | 90 |

EXAMPLE 2

Hybrids between M13mp9 clone II-16 DNA and radiolabeled 27 base oligomer were prepared by incubating 5 μg M13mp9 clone II-16 DNA with 64.5 ng oligomer in 0.5M NaCl, 10 mM Tris, pH 8.0, 1 mM Na₂EDTA at 65° C. for 10 minutes in a waterbath and subsequently allowing the waterbath temperature to slow cool to 30 ° C. At this time the hybrid DNA was purified over a Sepharose ® 4B column. The excluded hybrid DNA fractions were pooled and ethanol precipitated. Hybrid DNA was then resuspended to a concentration of 25 ng/μl in 10 mM Tris, pH 8.0, 1 mM Na₂EDTA. About 25 ng of reagent complex were subsequently incubated at 55° C. for 30 minutes or 3 hours in 10 μl of 2X SSC containing 0, 8, 10 or 12 percent polyethylene glycol (PEG), MW6000. All samples were prepared in duplicate with half receiving no addition of competitor DNA and the other half receiving 25 ng competitor M13mp8 clone 20 DNA. Following incubation, the samples were subjected to electrophoresis in 15% polyacrylamide slab gels. The resulting gels were autoradiographed at −80° C. with Kodak X-omat® film and Dupont® Cronex® intensifying screen, and scanned by densitometry.

After 30 minutes incubation at 55° C., the amount of 27 base oligomer DNA displaced from the probe DNA by competitor DNA increased as the percent PEG, MW6000 solution present in the reaction increased from 0 to 12 percent (Table 3). PEG, MW6000 alone did not cause dissociation of the oligomer DNA from the reagent complex in the first thirty minutes in the absence of M13mp8 clone 20 DNA (Table 3). After 3 hours incubation at 55° C., the amount of 27 base oligomer DNA found in the free form was still greater in the presence of PEG, MW6000, at all polymer concentrations than in its absence. The presence of PEG, MW6000, however, did cause substantial non-specific dissociation of hybridized 27 base oligomer DNA from the reagent complex in the absence of competitor M13mp8 clone 20 DNA and therefore conclusions about the specific effect of PEG in promoting strand displacement cannot be drawn for this lengthy period of incubation (see Example 6) (Table 3).

TABLE 3

| Minutes of Incubation | Percent (w/v) PEG, MW6000 | 25 ng Competitor DNA | Percent Free Oligomer |
|---|---|---|---|
| 30 | 0 | − | 0 |
|    |   | + | 0 |
|    | 8 | − | 0 |
|    |   | + | 68 |
|    | 10 | − | 0 |
|    |    | + | 100 |
|    | 12 | − | 0 |
|    |    | + | 100 |
| 180 | 0 | − | 0 |
|     |   | + | 72 |
|     | 8 | − | 47* |
|     |   | + | 100 |
|     | 10 | − | 67* |
|     |    | + | 100 |
|     | 12 | − | 32* |
|     |    | + | 100 |

*See Example 6, below, for a discussion of these values.

The effective weight percent range of PEG, MW6000 on strand displacement reactions was further studied in another experiment. Reagent complex hybrids were prepared and purified as described in Example 3, below. About 20 ng of reagent complex in 24 μl of 5X SSC were incubated at 52° C. for 90 minutes with 0 or 50 ng of competitor M13mp8 clone 20 DNA in the presence of 0, 5, 12 or 19% PEG, MW6000. The samples were then electrophoresed on a 15% polyacrylamide gel and the resulting gels subjected to autoradiography. Densitometric scans of the autoradiograms show that 5% PEG is ineffective in influencing the extent of strand displacement (Table 4) under these conditions while PEG concentrations of 12% and 19% significantly enhance strand displacement in a specific fashion.

TABLE 4

| Percent (w/v) PEG, MW 6000 | Competitor DNA Present | Percent Free Oligomer |
|---|---|---|
| 0 | − | 38 |
|   | + | 47 |
| 5 | − | 37 |
|   | + | 47 |
| 12 | − | 42 |
|    | + | 87 |
| 19 | − | 37 |
|    | + | 100 |

The significant weight percent range of PEG, MW6000 that enhanced strand displacement is thus at least 8–19% under these particular conditions (see 8% in Table 3). Example 8 and 11, below, shows effects at 2.5% and 5.0% PEG under different buffer conditions.

EXAMPLE 3

Hybrid DNA was made from ³²P-labelled 27 base oligomer (27-mer) and M13mp9 clone II-16 DNA which had been treated with the restriction enzyme HinfI. This enzyme cuts the M13mp9 DNA into several linear pieces without interrupting the region in M13mp9 clone II-16 containing the pBR322 DNA insert. The reaction mixture contained 0.8 pmoles of M13mp9 DNA and 6.8 pmoles of 27-mer in 77 μl of 5X SSC. The mixture was incubated at 50° C. for 30 minutes, then the mixture was fractionated using a Sepharose® CL-4B column connected to a fraction collector and an elution buffer of 10 mM Tris-HCl, pH 8.1, 1.0mM Na₂EDTA. Radioactivity was determined for each fraction by Cerenkov counting. The faster moving peak was pooled as the hybrid. About 45% of the M13mp9 DNA was hybridized to labeled oligomer.

The competition reaction mixtures consisted of 10 fmoles of the reagent complex, with or without circular competitor DNA, with or without E. coli rec A protein, and with or without PEG, MW 6000. The competitor DNA was 10 fmoles of M13mp8 clone 20 DNA. Rec A protein was present in amounts of either 143 ng or 1137 ng, which is 5 or 40 times the amount of hybrid DNA by weight. PEG, MW 6000 was present in some reaction mixtures. Competition reaction mixtures in rec A buffer (100 mM Tris-HCl, pH 7.5, 25 mM MgCl₂, 0.5 mg/ml bovine serum albumin, 1.5 mM dithiothreitol and 8 mM ATP) were incubated at 37° C. or 40° C. for 2.5 hours except for two controls which were not incubated at all. The competition results were analyzed by 15% polyacrylamide gel electrophoresis and autoradiography. The autoradiograms were evaluated on a Shimadzu CS930 thin layer chromatography plate scanner. The percents of unbound 27-mer are shown in Table 5.

There is no clear cut enhancement of competition by PEG, MW 6000 at either temperature and with or without rec A protein. Every sample with competitor DNA (#1–6 in Table 5) has more free oligomer at 40° C. than at 37° C. Rec A protein promotes competition at both temperatures, but favorable interaction with PEG, MW 6000 was observed only for sample #4 at 40° C. among these examples. In other experiments (not shown here but described in application Ser. No. 684,305, filed herewith, as Examples 8 and 14), 20% PEG, MW 6000 gave a more appreciable enhancement to observed levels of displacement in E. coli rec A protein-containing reaction mixtures under different conditions.

TABLE 5

| Sample | Competitor DNA | Rec A Protein | PEG 6000 | Percent Free Oligomer 37° C. | Percent Free Oligomer 40° C. |
|---|---|---|---|---|---|
| 1 | 26.7 ng | 0 | 0 | 23 | 44 |
| 2 | 26.7 ng | 0 | + | 37 | 43 |
| 3 | 26.7 ng | 142 ng | 0 | 41 | 54 |
| 4 | 26.7 ng | 142 ng | + | 27 | 81 |
| 5 | 26.7 ng | 1137 ng | 0 | 70 | 85 |
| 6 | 26.7 ng | 1137 ng | + | 65 | 73 |
| 7 | 0 | 0 | 0 | 0 | 6 |
| 8 | 0 | 0 | 0 | 6* | 6* |

*No incubation.

EXAMPLE 4

About 25 ng reagent complex DNA were prepared as described in Example 2 and were incubated at 55° C. for 60 minutes in 10 µl of 2X SSC containing 10% (w/v) polyethylene glycol of MW 200, 400, 1000, 3350, 6000 or 20,000 daltons. Samples were prepared in duplicate with half of the samples receiving 25 ng competitor M13mp8 clone 20 DNA and half receiving none. Following incubation for 60 minutes, all samples were subjected to electrophoresis in 15% polyacrylamide slab gels. The resulting gels were autoradiographed at −80° C. with Kodak® X-omat® film and a Dupont® Cronex® intensifying screen, and the autoradiograms were evaluated by densitometric scanning. Polyethylene glycols of molecular weights 3350, 6000 and 20,000 were more effective in enhancing competitive displacement of hybridized oligomer DNA than the polyethylene glycols of lower molecular weights (Table 6).

TABLE 6

| Polyethylene glycol MW | Percent Free Oligomer − competitor DNA | Percent Free Oligomer + Competitor DNA |
|---|---|---|
| 200 | 0 | 64 |
| 400 | 0 | 60 |
| 1,000 | 0 | 59 |
| 3,350 | 0 | 100 |
| 6,000 | 0 | 100 |
| 20,000 | 0 | 79 |
| Incubated Control, no Polyethylene Glycol | 0 | 24 |

EXAMPLE 5

Hybrids between M13mp9 clone II-16 DNA and the radiolabeled 27 base oligomer were prepared as described in Example 3. About 20 ng of reagent complex in 24 µl of 5X SSC were incubated in the absence or presence of 10% polyethylene glycol (PEG), MW6000 at 52° C. for 90 minutes with addition of 0, 2.0, 5.0, 20, 50, or 100 ng of competitor M13mp8 clone 20 DNA. All samples were immediately electrophoresed on 15% polyacrylamide slab gels and the resulting gels subjected to autoradiography. Densitometric scans of the autoradiograms show that the sensitivity of strand displacement reactions is enhanced by the inclusion of PEG, MW6000 (Table 7).

TABLE 7

| Inclusion of 10% PEG, MW6000 | Amount of Competitor DNA (in ng) | Percent Free Oligomer |
|---|---|---|
| − | 0 | 38 |
| − | 5.0 | 42 |
| − | 20 | 47 |
| − | 50 | 47 |
| − | 100 | 57 |
| + | 0 | 42 |
| + | 2.0 | 51 |
| + | 5.0 | 83 |
| + | 20 | 93 |
| + | 50 | 87 |
| + | 100 | 90 |

In a related experiment using a more highly purified reagent complex, reagent complex hybrids were prepared and purified as described in Example 2. About 25 ng hybrid DNA were then incubated in the presence of 10 µl 2X SSC and either 2.5, 6.25, 12.5, 25 or 50 ng competitor M13mp8 clone 20 DNA at 55° C. for 60 minutes, resulting in ratios of reagent complex DNA:competitor DNA of 1:0.1, 1:0.25, 1:0.5, 1:1.0 or 1:2.0, respectively. The samples were prepared in duplicate with half receiving 10% PEG, MW 6000 and half receiving none. Following incubation, the samples were subjected to electrophoresis on 15% polyacrylamide slab gels and the resulting gels were autoradiographed at −80° C. with Kodak X-omat film and a Dupont Cronex intensifying screen. Densitometric scans of the resulting autoradiogram demonstrate that, at all reagent complex DNA:competitor DNA ratios, specific disassociation of hybridized 27 base oligomer from probe DNA by competitor DNA was greater in the presence of 10% PEG, MW6000, than in its absence (Table 8).

TABLE 8

| Amount of reagent complex DNA (in ng) | Amount of competitor DNA (in ng) | % PEG, MW6000 | Percent Free Oligomer |
|---|---|---|---|
| 25 | 2.5 | 0 | 0 |
|  |  | 10 | 17 |
| 25 | 6.25 | 0 | 20 |
|  |  | 10 | 47 |
| 25 | 12.5 | 0 | 13 |
|  |  | 10 | 83 |
| 25 | 25 | 0 | 32 |
|  |  | 10 | 100 |
| 25 | 50 | 0 | 41 |
|  |  | 10 | 100 |

EXAMPLE 6

Control experiments were carried out to examine non-specific polyethylene glycol (PEG) interactions with reagent complex hybrids for strand displacement. In an initial experiment, hybrids between M13mp9 clone II-16 DNA and the 27 base perfectly matched oligomer were prepared and purified as described in Example 2. About 225 ng hybrid DNA were incubated at 55° C. in 90 μl of 2X SSC containing 10% (w/v) PEG, MW 6000. Aliquots of 10 μl were removed at the start of the experiment and at 30, 90 and 150 minutes. The aliquots were subjected to electrophoresis on 15% polyacrylamide slab gels, the resulting gels were autoradiographed at −80° C. and the autoradiograms obtained were evaluated by densitometric scanning using a Shimadzu CS930 plate scanner. The reagent complex was stable as a hybrid DNA under these incubation conditions for up to 2½ hours (Table 9).

TABLE 9

| Hours of Incubation | Percent Free Oligomer |
|---|---|
| 0 | 0 |
| 0.5 | 0 |
| 1.5 | 0 |
| 2.5 | 0 |

This experiment was terminated at 2.5 hours. In other experiments where mixtures with 10% PEG went for 3 hours (including the experimental values shown by asterisks in Table 3, above), non-specific dissociation of reagent complex hybrids was observed at 3 hours. Rather than attempt to understand this anomalous result, experiments conducted afterwards by the same group were terminated in less than 3 hours.

In a related experiment to study potential aggregation of oligomer and polyethylene glycol (PEG), MW 6000, 0.15 pmole of radiolabeled oligomer was incubated in 20 μl 2X SSC or 5X SSC for 30, 90 or 150 minutes with or without 10% (w/v) PEG 6000 and then analyzed by gel electrophoresis and autoradiography and densitometric scanning (Table 10). These results demonstrate that oligomer does not spontaneously associate with PEG 6000 and remove the possibility that observed decreases in free oligomer from unpurified reagent complex preparations are artifactual.

TABLE 10

| Minutes of Incubation | 10% PEG | SSC Concentration | Percent Free Oligomer |
|---|---|---|---|
| 30 | + | 2X | 100 |
|  |  | 5X | 100 |
| 90 | + | 2X | 100 |
|  |  | 5X | 100 |
| 150 | − | 2X | 100 |
|  |  | 5X | 100 |
|  | + | 2X | 93 |
|  |  | 5X | 97 |

EXAMPLE 7

About 25 ng of reagent complex (hybrid DNA produced when M13mp9 clone II-16 DNA was hybridized with the $^{32}$P end-labeled perfect match 27-mer DNA) in 2x SSC and a molar excess of unhybridized excess $^{32}$P end-labeled perfect match 27-mer DNA were combined in the presence or absence of 10% polyethylene glycol (PEG), MW 6000. The mixture was then passed through a 5.0 ml Sepharose® 4B column in 10 mM Tris, pH 8.0, 1 mM Na$_2$EDTA to determine whether the presence of 10% PEG (MW 6000) in the sample interfered with the column separation of the larger hybrid DNA from the smaller 27 mer DNA or the column elution profile. The elution profiles demonstrated no significant distortion due to the presence of 10% PEG (MW 6000), indicating that post-displacement separation and/or quantitation of free oligomer from reactions in the presence of 10% (w/v) PEG, MW 6000, can successfully be carried out on fractions collected from gel permeation chromatography trials.

EXAMPLE 8

A $^{32}$P-labeled fragment of pBR322 DNA was annealed to an M13 clone containing a cloned complementary region prepared in the following manner. A portion of pBR322 (about 650 bases in length) located between the unique Eco RI and Sal I restriction sites was cloned into M13mp8 or M13mp11l by conventional methods. Using a $^{32}$P-end labeled 27 nucleotide long oligonucleotide complementary to a portion of this pBR322 sequence as primer and the appropriate template chosen from the above two clones, DNA synthesis was initiated on the template and extended partially around the circle. The DNA was digested with Eco RI and the resulting 375 nucleotide end-labeled fragment was purified by denaturing agarose gel electrophoresis. This 375-mer was annealed back to the pBR322/M13 probe strand to form a reagent complex wherein the labeled polynucleotide was bound to the end 375 nucleotides of a 650 nucleotide target binding region. Unannealed 375-mer was removed by a Sepharose® CL-4B column.

The reagent complex (10 ng) was mixed in hybridization buffer with either 10 or 100 ng of a circular DNA strand (i.e., as a part of a pBR322 Eco RI-SalI insert in M13 bacteriophage) or linearized DNA strand of the opposite sense as competitor DNA. The displacement was carried out at 80° C. for 5, 15, 30, or 60 minutes and in the presence or absence of 10% (w/v) PEG, MW 6000. The results were analyzed by gel electrophoresis and autoradiography. The rate of displacement in the presence of 10% PEG, MW 6000 was at least ten-fold greater at short times of incubation (e.g., 5 minutes) than in the absence of PEG, MW 6000. After 60 minutes of reaction, however, an unexpected result was observed. The displaced DNA band disappeared from the autoradiogram, and most radiolabeled material migrated at the top of the gel. The explanation appears to be some sort of aggregation effect based on subsequent control experiments.

EXAMPLE 9

An 840 base pair Eco Rl-Bgl II restriction fragment containing the first 262 codons of the human serum albumin gene was subcloned into the single-stranded phage vector M13mp9, generating the clone designated M13mp9-albumin. (See Lawn et al., *Nucleic Acid Research* 9: 6103–6114 (1981) for the DNA sequence of the human albumin gene). Also inserted into this vector was the Eco RI fragment containing the polylinker from M13mp7. This polylinker sequence, inserted adjacent to the albumin sequence at the Eco RI site, is capable of forming a double-stranded hairpin structure in the otherwise single-stranded molecule. Cleavage of such a molecule with the enzyme Bam HI results in a linear and full length single-stranded molecule. 14 base long oligonucleotide (5' end-GATGCACACAAGAG-3' end) was kinased using $^{32}$p-$\gamma$-ATP, hybridized to sequences within the albumin insert, and extended *in vitro* using *E. coli* DNA polymerase. The resulting DNA molecules were then digested with Pvu II, which cuts once in the human albumin insert. The final labeled polynucleotide, a 175 base long labeled and single stranded molecule, was then purified by electrophoresis on a denaturing agarose gel. The purified labeled polynucleotide was hybridized to the above M13mp9-albumin strand which serves as the probe polynucleotide; the probe used was either circular or had been linearized with Bam HI. Unhybridized labeled polynucleotide was removed from the reagent complex by passage over two successive Sepharose ® CL-4B columns.

Model competitor DNAs used in displacement experiments were either the complementary DNA strand to the human albumin sequence of the M13mp9-albumin clone inserted in an M13mp8 vector (and hereafter designated as M13mp8-albumin), or a denatured double-stranded 840 base pair Eco RI-Bgl II fragment which is colinear with the insert in the M13mp9-albumin clone.

Displacements were carried out by incubating of approximately 10 ng of reagent complex with 100 ng of analyte DNA in 0.2M NaCl, 100 mM Tris, pH 8.0, at 85° C. for 5, 15, 30 and 60 minutes. At appropriate times, samples were placed on ice to stop the reaction, and then all samples were run on a 1.5% agarose gel to assess displacement efficiency.

In the absence of analyte, no melting of the probe-template complex was observed at 5, 15 or 30 minutes, although at 60 minutes approximately 10% of the probe was melted at this temperature. The addition of a tenfold excess of analyte to the displacement reaction resulted in the displacement of approximately 50% of the probe at 15 minutes, 75% at 30 minutes and 95% at 60 minutes. The addition of 2.5% (w/v) PEG, MW 6000 to the reaction mix enhanced the displacement rate twofold; approximately 95% displacement occurred during 30 minutes incubation. The addition of 5% (w/v) PEG, MW 6000 to the reaction further increased the rate of the displacement reaction significantly: displacement was essentially complete within 15 minutes. The addition of 10% (w/v) PEG, MW 6000 also apparently enhanced the rate of the displacement still further, although the extent of this enhancement could not be accurately estimated from the autoradiograph due to a gel artifact frequently observed with high concentrations of PEG at high temperature in this buffer system. Although this experiment did not include controls of displacement complex without competitor, but in the presence of PEG, the experiment of Example 8 did include such a control. In that experiment, incubation under similar conditions to those of this Example with 10% (w/v) PEG, MW 6000 caused no detectable non-specific melting (dissociation) of the reagent complex in up to 60 minutes of incubation. Thus, increasing concentrations of PEG (at 85° C.) appear to specifically increase the rate of the hybridization-strand displacement.

EXAMPLE 10

This experiment was done to determine if a nonionic polymer, FICOLL, MW 400,000 (purchased from Sigma, but Pharmacia's trademark) would have a similar enhancing effect on the nucleic acid strand displacement reaction as did PEG. The displacement complex, analyte DNA, and reaction conditions were those described in Example 8. The displacement reaction mixtures were incubated at 80° C. for 5, 15, 30 or 60 minutes in the presence or absence of the FICOLL polymer. The addition of 10 ng of analyte DNA to approximately 10 ng of reagent complex, in the absence of FICOLL resulted in the displacement of about 50% of the labeled polynucleotide (end-labeled 375-mer) in 30 minutes and of all detectable labeled polynucleotide in 60 minutes of incubation. The addition of 2% (w/v) or 4% (w/v) FICOLL to the reaction enhanced the rate of displacement slightly, with approximately 75–80% displacement occurring in 30 minutes, although non-specific effects cannot be ruled out at this time. This experiment suggests that FICOLL polymer and similar non-ionic reaction products of a sugar with epichlorohydrin may be useful for increasing the reaction rate.

EXAMPLE 11

A reagent complex was prepared as in Example 4 of parent application U.S. Ser. No. 607,885 having a 1.1 kb albumin insert within M13 bacteriophage as the target binding region and an end-labeled 32-mer oligomer as the labeled polynucleotide. 10 ng of this reagent complex was combined with either:

(a) 100 ng of boiled plasmid pAlb5 digested with PstI and Bgl II containing an albumin coding sequence complementary to part of the albumin insert in the probe (including the 32 bases bound to 32-mer); or (b) 100 ng of boiled plasmid pUC8 digested with TaqI (this sequence is non-complementary and thus serves as a negative control).

The samples were combined in a 10 μl volume containing 50mM Tris, 1M NaCl and either 0, 5, 10, 15 or 20% PEG, MW 6000. Following incubations for 10 minutes at 50° C., the samples were immediately quenched in a dry ice/ethanol bate, thawed on ice and electrophoresed on a 2.5% agarose gel and autoradiographed. The amounts of displaced polynucleotides were estimated visually, as shown in Table 11. The results show no detectable displacement in the absence of the specific analyte at any PEG concentration and a significant enhancement in the amount of displaced labeled polynucleotide in 10 minutes under these conditions in the presence of the specific analyte when 5 or 10% (w/v) PEG, MW 6000 was also present.

TABLE 11

| % PEG, MW 6000 | Non-Specific Competitor | Specific Competitor |
|---|---|---|
| 0 | ND | 10% |

TABLE 11-continued

| % PEG, MW 6000 | Non-Specific Competitor | Specific Competitor |
| --- | --- | --- |
| 5 | ND | 40% |
| 10 | ND | 50% |
| 15 | ND | 20% |
| 20 | ND | 5% |

ND = not detectable, i.e. <2%

What is claimed is:

1. A method for determining the presence of a predetermined target nucleotide sequence in the nucleic acid of a biological sample which comprises the steps:
   (a) providing a reagent complex of (i) a probe polynucleotide which is capable of base pair binding via hydrogen bonds of purine/pyrimidine bases to the target nucleotide sequence, and (ii) a labeled polynucleotide which is bound by base pair binding via hydrogen bonds of purine/pyrimidine base pairs to the probe polynucleotide in a region of the probe polynucleotide of at least about 20 nucleotides at least partially coextensive with the region in which the probe polynucleotide is capable of binding to the target nucleotide sequence;
   (b) contacting the reagent complex with a biological sample in the presence of a polyether polymer under conditions in which the target nucleotide sequence, if present in the biological sample, binds to the probe polynucleotide and displaces labeled polynucleotide from the complex, the polyether polymeric agent being of a molecular weight and at a concentration sufficient to increase the rate of appearance of displaced labeled polynucleotide; and
   (c) determining the presence of labeled polynucleotide displaced from the reagent complex.

2. The method of claim 1 wherein the labeled polynucleotide is a polynucleotide bonded to an enzyme label.

3. The method of claim 1 wherein the probe polynucleotide contains a target binding region capable of base pair binding to the target nucleotide sequence and a labeled polynucleotide binding region bound to bases of the labeled polynucleotide in the complex, and wherein the labeled polynucleotide binding region is contained within the target binding region.

4. The method of claim 3 wherein the labeled polynucleotide binding region is adjacent to one end of the target binding region.

5. The method of claim 4 wherein the labeled polynucleotide binding region is about 20 to about 500 nucleotides in length.

6. The method of claim 5 wherein the portion of the target binding region that is not part of the labeled polynucleotide region is at least about 100 nucleotides in length.

7. The method of claim 1 wherein the probe polynucleotide is immobilized to a solid support in the reagent complex.

8. The method of claim 7 wherein the probe polynucleotide is covalently linked to the solid support in the reagent complex.

9. The method of claim 7 wherein the determining step (c) comprises:
   (c1) separating a first phase containing immobilized probe polynucleotide from a second phase comprising displaced labeled polynucleotide; and
   (c2) determining the presence of labeled polynucleotide in the second phase.

10. The method of claim 9 wherein the probe polynucleotide contains a target binding region capable of base pair binding to the target nucleotide sequence and a labeled polynucleotide binding region bound by purine/pyrimidine base pairing to bases of the labeled polynucleotide in the complex, and wherein the labeled polynucleotide binding region is contained within the target binding region.

11. The method of claim 10 wherein the probe polynucleotide is attached to the solid substrate adjacent to one end of the probe polynucleotide and the target binding region is adjacent to the opposite end of the probe polynucleotide.

12. The method of claim 1 wherein the reagent complex is free in solution during the contacting step (b).

13. The method of claim 12 wherein the determining step (c) comprises:
   (c1) separating the reagent complex remaining from a portion of the reaction solution after the contacting step (b), and
   (c2) determining the presence of any displaced labeled polynucleotide in a solution phase after separation.

14. The method of claim 1 wherein the polyether polymer is poly(propylene glycol).

15. The method of claim 1 wherein the polyether polymer is a poly(alkylene oxide) of the formula $H(O-R)_n$ wherein R is an alkylene moiety of 1–6 carbons and n is an integer, on a weight average molecular weight basis, of about 35 to about 690.

16. The method of claim 1 wherein the polyether polymer is poly(ethylene oxide).

17. The method of claim 16 wherein the poly(ethylene oxide) is of weight average molecular weight of at least about 1500.

18. The method of claim 16 wherein the poly(ethylene oxide) is of weight average molecular weight of at least about 2500.

19. A diagnostic kit for determining the presence of a predetermined target nucleotide sequence in the nucleic acid of a biological sample comprising:
   (a) the reagent complex of:
      (i) a probe polynucleotide which is capable of base pair binding via hydrogen bonds of purine/pyrimidine base pairs to the target nucleotide sequence, and
      (ii) a labeled polynucleotide which is bound by base pair binding via hydrogen bonds of purine/pyrimidine base pairs to the probe polynucleotide in a region of the probe polynucleotide of at least about 20 nucleotides at least partially coextensive with the region in which the probe polynucleotide is capable of base pair binding to the target nucleotide sequence;
      the potential base pair binding between the target nucleotide sequence and the probe polynucleotide being capable of displacing the labeled polynucleotide from the reagent complex, and
   (b) a volume-excluding inert polymeric agent which is non-ionic or anionic of sufficient molecular weight and amount relative to the reagent complex to increase the rate of appearance of displaced labeled polynucleotide.

20. The diagnostic kit of claim 19 wherein the region of the probe polynucleotide to which the labeled polynucleotide is bound is about 20 to about 1000 nucleotides in length.

21. A diagnostic kit for determining the presence of a predetermined target nucleotide sequence in the nucleic acid of a biological sample comprising:
   (a) the reagent complex of:
      (i) a probe polynucleotide which is capable of base pair binding via hydrogen bonds of purine/pyrimidine base pairs to the target nucleotide sequence, and
      (ii) a labeled polynucleotide which is bound by base pair binding via hydrogen bonds of purine/pyrimidine base pairs to the probe polynucleotide in a region of the probe polynucleotide of at least about 20 nucleotides at least partially coextensive with the region in which the probe polynucleotide is capable of base pair binding to the target nucleotide sequence;
   the potential base pair binding between the target nucleotide sequence and the probe polynucleotide being capable of displacing the labeled polynucleotide from the reagent complex, and
   (b) a polyether polymer of sufficient molecular weight and amount relative to the reagent complex to increase the rate of appearance of displaced labeled polynucleotide.

22. The diagnostic kit of claim 21 wherein the polyether polymer agent is a poly(alkylene oxide) of the formula $H(O-R)_n-H$ wherein R is alkylene of 1-6 carbons and n is an integer, on a weight average basis, of about 35 to about 690.

23. The diagnostic kit of claim 21 wherein the polyether polymer is poly(ethylene oxide).

24. The diagnostic kit of claim 21 wherein the poly(ethylene oxide) is of weight average molecular weight at least about 1500.

25. The diagnostic kit of claim 24 wherein the poly(ethylene oxide) is of weight average molecular weight at least about 2500.

26. The diagnostic kit of claim 21 wherein the polyether is poly(propylene glycol).

27. A method for determining the presence of a predetermined target nucleotide sequence in the nucleic acid of a biological sample which comprises the steps:
   (a) providing a reagent complex of (i) a probe polynucleotide which is capable of base pair binding via hydrogen bonds of purine/pyrimidine bases to the target nucleotide sequence, and (ii) a labeled polynucleotide which is bound by base pair binding via hydrogen bonds of purine/pyrimidine base pairs to the probe polynucleotide in a region of the probe polynucleotide of at least about 20 nucleotides at least partially coextensive with the region in which the probe polynucleotide is capable of binding to the target nucleotide sequence;
   (b) contacting the reagent complex with a biological sample in the presence of a volume-excluding inert polymeric agent which is non-ionic or anionic under conditions in which the target nucleotide sequence, if present in the biological sample, binds to the probe polynucleotide and displaces labeled polynucleotide from the complex, the volume-excluding inert polymeric agent being of a molecular weight and at a concentration sufficient to increase the rate of appearance of displaced labeled polynucleotide; and
   (c) determining the presence of labeled polynucleotide displaced from the reagent complex.

28. The method of claim 27 wherein the volume-excluding inert polymeric agent is non-ionic.

29. The method of claim 27 wherein the non-ionic volume excluding inert polymer is the reaction product of a sugar with epichlorohydrin.

30. The method of claim 27 wherein the volume-excluding inert polymer is anionic.

31. A method for determining the presence of a predetermined target nucleotide sequence in the nucleic acid of a biological sample which comprises the steps:
   (a) providing a reagent complex of (i) a probe polynucleotide which is capable of base pair binding via hydrogen bonds of purine/pyrimidine bases to the target nucleotide sequence, and (ii) a labeled polynucleotide which is bound by base pair binding via hydrogen bonds of purine/pyrimidine base pairs to the probe polynucleotide in a region of the probe polynucleotide of at least about 20 nucleotides at least partially coextensive with the region in which the probe polynucleotide is capable of binding to the target nucleotide sequence;
   (b) contacting the reagent complex with a biological sample in the presence of a polyether polymer under conditions in which the target nucleotide sequence, if present in the biological sample, binds to the probe polynucleotide and displaces labeled polynucleotide from the complex, the polyether polymeric agent being of a molecular weight and at a concentration sufficient to increase the rate of appearance of displaced labeled polynucleotide; and
   (c) determining the presence of labeled polynucleotide remaining in the reagent complex.

* * * * *

UNITED STATES PATENT AND TRADEMARK OFFICE
CERTIFICATE OF CORRECTION

PATENT NO. : 4,766,064

DATED : August 23, 1988

INVENTOR(S) : Jon I. Williams  et al

It is certified that error appears in the above-identified patent and that said Letters Patent is hereby corrected as shown below:

The Notice should read:

--The portion of the term of this patent subsequent to August 23, 2005 has been disclaimed.--

Signed and Sealed this

First Day of August, 1989

Attest:

DONALD J. QUIGG

*Attesting Officer*    *Commissioner of Patents and Trademarks*